US 7,073,499 B1

(12) United States Patent
Reinhold et al.

(10) Patent No.: US 7,073,499 B1
(45) Date of Patent: Jul. 11, 2006

(54) INHALER WITH AIRFLOW REGULATION

(75) Inventors: Olaf Reinhold, San Diego, CA (US); Robert P. Lackey, Carlsbad, CA (US); Jeffrey P. Taub, Escondido, CA (US)

(73) Assignee: Injet Digital Aerosols Limited, New South Wales (AU)

( * ) Notice: Subject to any disclaimer, the term of this patent is extended or adjusted under 35 U.S.C. 154(b) by 113 days.

(21) Appl. No.: 10/062,174

(22) Filed: Jan. 31, 2002

Related U.S. Application Data

(60) Provisional application No. 60/266,757, filed on Feb. 6, 2001, provisional application No. 60/266,062, filed on Feb. 6, 2001, provisional application No. 60/266,675, filed on Feb. 6, 2001, provisional application No. 60/267,091, filed on Feb. 6, 2001.

(51) Int. Cl.
*A61M 11/00* (2006.01)

(52) U.S. Cl. .................. 128/200.18; 128/200.23; 128/200.14; 128/200.21

(58) Field of Classification Search ........... 128/200.14, 128/200.18, 200.19, 200.21, 200.22, 200.23, 128/203.12, 203.15, 203.23, 204.25, 205.24
See application file for complete search history.

(56) References Cited

U.S. PATENT DOCUMENTS

| | | | |
|---|---|---|---|
| 3,818,908 A | 6/1974 | Phillips | 128/173 |
| 3,900,138 A | 8/1975 | Phillips | 222/340 |
| 4,368,850 A | 1/1983 | Szekely | 239/333 |
| 4,454,877 A | 6/1984 | Miller et al. | 128/200.21 |
| 5,161,524 A | 11/1992 | Evans | 128/203.15 |
| 5,363,842 A | 11/1994 | Mishelevich et al. | 128/200.14 |
| 5,364,838 A | 11/1994 | Rubsamen | 514/3 |
| 5,437,271 A * | 8/1995 | Hodson et al. | 128/203.15 |
| 5,505,195 A | 4/1996 | Wolf et al. | 128/203.15 |
| 5,655,520 A | 8/1997 | Howe et al. | 128/203.12 |
| 5,727,546 A | 3/1998 | Clarke et al. | 128/203.15 |
| 5,809,997 A | 9/1998 | Wolf | 128/200.23 |
| 5,894,841 A | 4/1999 | Voges | 128/203.12 |
| 5,896,853 A | 4/1999 | Howlett | 128/200.23 |
| 5,941,240 A | 8/1999 | Gonda et al. | 128/200.14 |
| 5,975,076 A | 11/1999 | Yianneskis et al. | 128/203.15 |
| 6,003,513 A | 12/1999 | Readey et al. | 128/205.24 |
| 6,014,970 A | 1/2000 | Ivri et al. | 128/200.16 |
| 6,029,662 A | 2/2000 | Marcon | 128/203.15 |

(Continued)

FOREIGN PATENT DOCUMENTS

CA 2146954 10/1996

(Continued)

*Primary Examiner*—Henry Bennett
*Assistant Examiner*—Andrew Bunin
(74) *Attorney, Agent, or Firm*—Marsh Fischmann & Breyfogle LLP

(57) ABSTRACT

The present invention is generally directed to a respiratory delivery system (e.g. an inhaler) used to discharge an appropriate substance therefrom for inhalation by a user. The respiratory delivery system generally has at least one airflow inlet, at least one outlet (e.g., mouthpiece, nasal mask), at least one airflow passage extending therebetween, and at least one ejection actuator for discharging an appropriate substance into the airflow. The respiratory delivery system also generally includes an airflow regulation assembly that can adjust the size of a passage through which substantially all of the airflow is directed to achieve/maintain a certain flow rate through the inhaler.

31 Claims, 9 Drawing Sheets

U.S. PATENT DOCUMENTS

| | | | |
|---|---|---|---|
| 6,044,841 A | 4/2000 | Verdun et al. | 128/200.18 |
| 6,073,629 A | 6/2000 | Hardy et al. | 128/203.15 |
| 6,085,742 A * | 7/2000 | Wachter et al. | 128/200.23 |
| 6,148,815 A | 11/2000 | Wolf | 128/205.23 |
| 6,196,218 B1 * | 3/2001 | Voges | 128/200.14 |
| 6,202,642 B1 | 3/2001 | McKinnon et al. | 128/200.23 |
| 6,205,999 B1 | 3/2001 | Ivri et al. | 128/200.22 |
| 6,443,151 B1 | 9/2002 | Ruskewicz | 128/203.15 |

FOREIGN PATENT DOCUMENTS

| | | |
|---|---|---|
| WO | WO 02/15968 | 2/2002 |

\* cited by examiner

INHALER WITH AIRFLOW REGULATION

RELATED APPLICATIONS

This application claims priority under 35 USC 119(e) to U.S. Provisional Application Nos. 60/266,757 entitled Inhaler with Airflow Regulation; 60/266,062 entitled Inhaler with Ejection Actuator Operational Test System/Method; 60/266,675 entitled Test Protocol for Inhaler with Multiple Ejection Actuators; and 60/267,091 entitled Inhaler with Electronic-Pulse Multi Actuator Delivery Control; all of which were filed Feb. 6, 2001, and all of which are incorporated herein by reference in their entireties.

FIELD OF THE INVENTION

The present invention generally relates to the field of inhalers which deliver an appropriate substance to a user typically during inspiration and, more particularly, to an inhaler which adjusts the size of an airflow passage to achieve/maintain a certain flow rate.

BACKGROUND

Respiratory delivery systems, such as metered dose inhalers, dry powder inhalers, and nebulizers, generally make it possible to introduce substances to pulmonary tissue of the body usually via simple inhalation. Metered dose inhalers generally combine a medicament and a propellant in a pressurized aerosol container equipped with valve to release a metered dose of aerosol into an inhaled airstream upon actuation of the container. Dry powder inhalers usually utilize bursts of inspired air to fluidize powdered doses of medicament and draw these powdered doses into the respiratory tract. Nebulizers generally form an aerosol by atomizing a medicament in a substantially continuous carrier gas stream which can then be inhaled.

Regardless of the respiratory delivery system utilized, conventional introduction of medicament to the pulmonary tissue of the human body has much to be desired in the way of successfully delivering a selected/predetermined amount of medicament to the pulmonary tissue of an individual regardless of the relative strength/weakness of that individual's respiratory system. For example, current metered dose inhalers generally require at least some synchronization between valve actuation and the user's inhalation (which has proven difficult for some users). Since metered dose inhalers generally depend on a minimum threshold inhalation by the user, an inhalation which is below that minimum threshold can result in less than the required amount of medicament successfully reaching the pulmonary tissues. Accordingly, various attempts have been made to develop metered dose inhalers which "sense" the amount of airflow during inhalation and vary the amount of drug dispensed based on the flow rate of the inhalation. In other words, in an exemplary situation in which two individuals utilize metered dose inhalers equipped with such "sensors", a first individual (who can inhale with less strength than a second individual) will have a greater concentration of medicament dispensed with every actuation than the second individual will have. However, such attempts at regulating amounts of medicament to depend on the strength of the user's inhalation have resulted in varying degrees of success, all of which tend to provide a hefty price tag for the consumer.

Dry powder inhalers at least generally tend to avoid the synchronization problem of metered dose inhalers. However, dry powder inhalers also fail to solve the problem of varied magnitudes of inhalation from user to user, and (regarding the same user) from situation to situation. In other words, an individual may not be capable of effecting an inhalation that has enough force to "fluidize" and inspire the entire amount of powdered medicament. Accordingly, the dose(s) of powdered medicament which actually reaches the pulmonary tissue tends to vary based on the force of inspiration.

As for nebulizers, inhalation generally tends to reduce pressure at the nebulizer nozzle; accordingly, the desired dosage of medicament is generally influenced by the duration and strength of the user's inhalation. While most nebulizers function on a "continuous stream of vapor" basis, control systems have been utilized to direct the aerosolized gas flow from the nebulizer to a "holding chamber" from which the user may draw a charge. However, these "charges" are still generally dependent upon a user being able to inspire the entire amount of vaporized medicament from the holding chamber. Accordingly, a user having relatively weak inhalation capabilities may not receive the entire "charge" of medicament. Thus, varying degrees of success have also been observed with regard to nebulizers that attempt to control the amount of dispensed medicament with respect to a user's inhalation strength.

In summary, the precision of dose delivery in conventional respiratory delivery systems is undesirably imprecise. In each of the above-discussed systems, the desired amount of medicament to be delivered to the intended pulmonary tissue is generally dependent (at least to some degree) on the user's strength of inhalation, and is generally variable from dose to dose and/or person to person. In other words, a correlation has been allowed to exist between a user's lack (or variation) of breathing capability and a lack (or variation) of that user consistently receiving the adequate, prescribed, and/or desired amount of medicament. Accordingly, it would be desirable to develop an improved respiratory delivery system that exhibits effective entrainment of a non-varying amount of dispensed medicament into the airstream and successful delivery of such a non-varying amount of dispensed medicament to the target pulmonary tissue.

SUMMARY OF THE INVENTION

The claims in the subject patent application are generally directed to the first family of embodiments discussed in the Preface to the Detailed Description section of the present patent application.

DETAILED DESCRIPTION

Preface

Figures 1, 2:
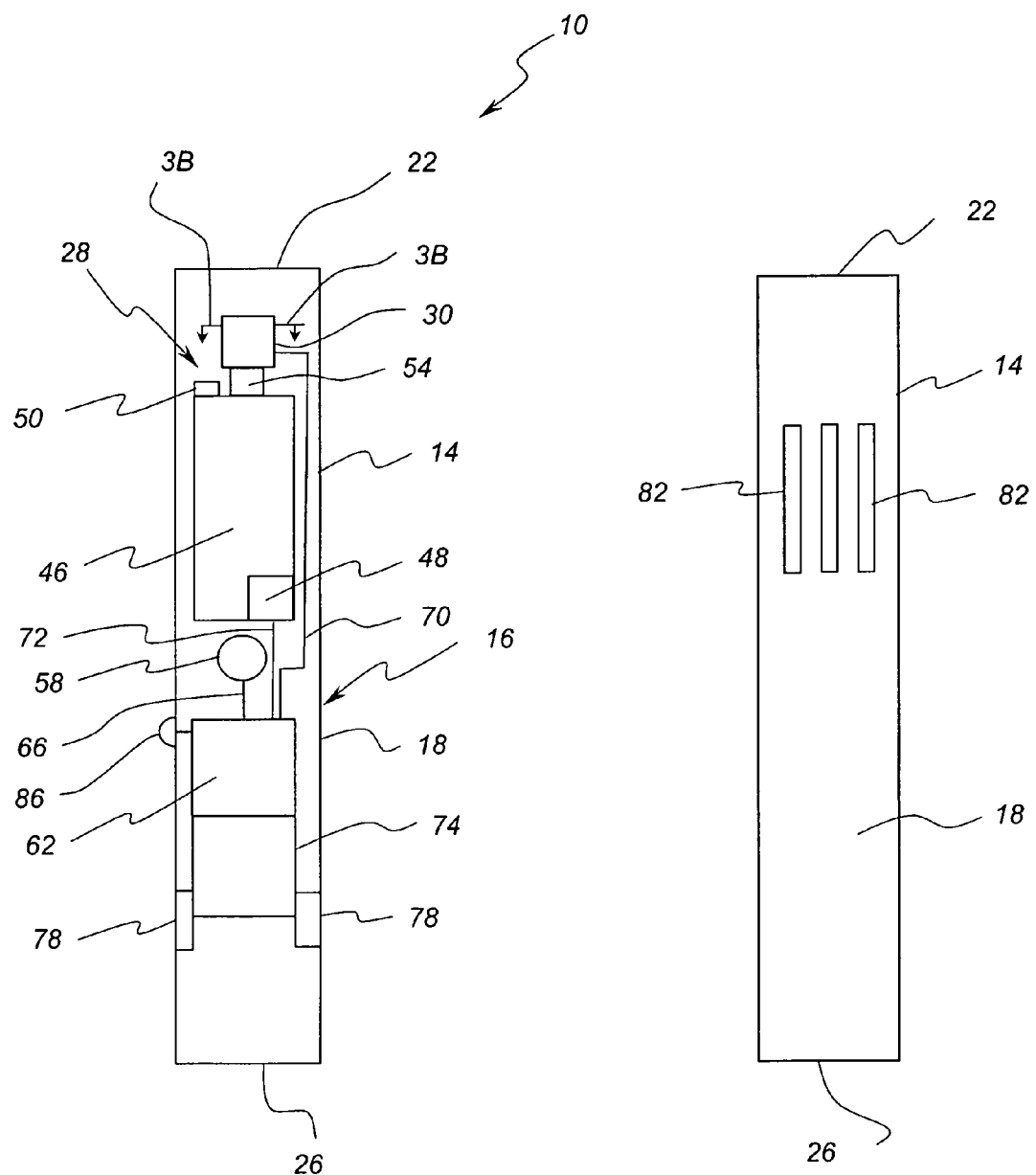
FIG. 1 is a cutaway view of one embodiment of an inhaler.
FIG. 2 is a side view of the inhaler of FIG. 1.
Figure 3A:
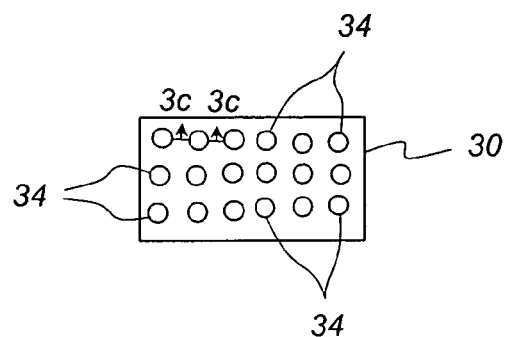
FIG. 3A is an end view of a droplet ejection device used by the inhaler of FIG. 1.
Figure 3B:
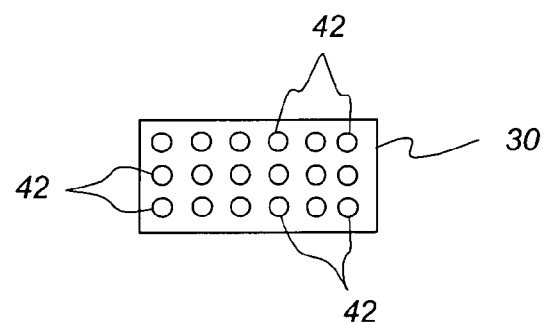
FIG. 3B is a cross-sectional view of the droplet ejection device of FIG. 1, taken along line 3B—3B in FIG. 1.
Figure 3C:
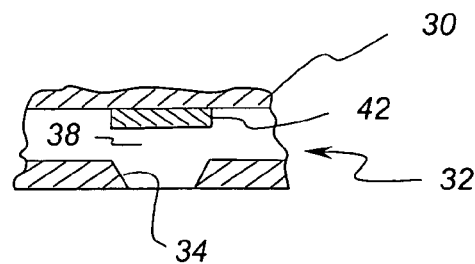
FIG. 3C is a cross-sectional view of one embodiment of a droplet ejection device which may be used by the inhaler of FIG. 1, and which may then be in accordance with the cross-section noted by line 3C—3C in FIG. 3A.

As an introduction to the various families of embodiments of the present invention, both oral and nasal inhalations are generally encompassed by the present invention. One common substance that may be dispensed, discharged, or otherwise ejected by inhalers of the present invention is a liquid medicament that can be ejected in the form of a plurality of individual and discrete droplets, typically into the airflow through the inhaler somewhere upstream of its discharge outlet(s). However, the present invention is not limited to any particular type of substance that is being ejected by the inhaler and further is not limited to any particular form in which this substance may be ejected from the inhaler.

A first family of embodiments of the present invention is generally directed to an inhaler that is used to discharge an appropriate substance therefrom for inhalation by a user. A first aspect of this first family of embodiments is embodied by an inhaler that includes at least one airflow inlet, at least one outlet (e.g., mouthpiece, nasal mask), and at least one airflow passage extending therebetween. The inhaler also includes at least one ejection actuator and an airflow regulation assembly. Generally, the ejection actuator(s) discharges an appropriate substance into the airflow, while the airflow regulation assembly adjusts the size of a passage through which all of the airflow is directed to achieve/maintain a certain flow rate through the inhaler.

Various refinements exist of the features noted in relation to the first aspect of the first family of embodiments. Further features may also be incorporated in the first aspect of the first family of embodiments as well. These refinements and additional features may exist individually or in any combination. Any type of ejection actuator may be utilized by the inhaler of the first aspect. Multiple ejection actuators may be utilized as well. These multiple ejection actuators may be independently actuatable. These multiple ejection actuators also may be separated into a plurality of groups, with each individual group of ejection actuators being independently actuatable.

In one embodiment, the airflow regulation assembly includes a flow regulation port of a certain length and with an inner diameter which changes over its length. For instance, the flow regulation port may at least generally converge in the direction of the airflow therethrough. All of the airflow is directed through this flow regulation port. A baffle, piston, or the like is movably disposed within the noted inlet port and in spaced relation to an inner wall of the inlet port over at least a portion of the length of the inlet port. Any "flow throttling" structure may be utilized. Movement of the baffle relative to the flow regulation port changes the size of the spacing between the baffle and the inner wall of the flow regulation port.

The above-noted change in the size of the spacing between the baffle and the inner wall of the flow regulation port may be utilized to realize a certain flow rate for the airflow through the inhaler. It may be preferable to have a certain flow rate of air being drawn through the inhaler for enhancing the delivery of the inhaled substance. More specifically, delivery of the inhaled substance may be enhanced by providing some relationship between the flow rate of the air being drawn through the inhaler and the velocity at which the substance (e.g., medicament) is ejected or discharged into the airflow. Assuming that a user is able to generate at least a certain threshold level of inhalatory forces, the baffle may be positioned relative to the flow regulation port to realize a certain flow rate through the inhaler, regardless of the inhalatory forces that are being generated by the user.

Movement of the above-noted the baffle may be realized by a purely mechanical system. For instance, a biasing member (e.g., coil spring) may act on the baffle so as to oppose the inhalation forces which are being exerted on the baffle. That is, the baffle may be biased in the "upstream" direction. Inhalatory forces below a certain level will not compress the biasing member so as to maintain a maximum spacing between the baffle and the inner wall of the noted converging flow regulation port. However, once inhalatory forces exceed a certain level, the biasing member will begin to compress to reduce the spacing between the baffle and the inner wall of the inlet port. This reduction of the size of the airflow passage through which all airflow must pass will therefore only allow for a certain maximum flow rate of the airflow through the inhaler. Further increases in the inhalatory forces will further reduce the spacing between the baffle and the inner wall of the noted converging flow regulation port such that the flow rate through the inhaler is maintained at least substantially at the noted certain maximum flow rate. Stated another way, so long as the inhalatory forces are in excess of a certain threshold, any inhalatory force by a user will produce at least substantially the same flow rate through the inhaler as a result of the modification of the size of the airflow passage through which all airflow is directed (e.g., by changing the position of the baffle in the converging flow regulation port). There may be other ways to adjust the size of an airflow passage through which all airflow is directed via a purely mechanical system and which are within the scope of the first aspect of this first family of embodiments. However, the structure described herein may provide one or more benefits or advantages based upon its unique design.

Movement of the noted baffle relative to the noted flow regulation port may also be accomplished in response to some type of signal. For instance, the subject first aspect may further include an airflow monitoring assembly to allow for a determination of the flow rate through at least a portion of the inhaler. Flow rate information may be used to determine the size of the spacing between the baffle and the inner wall of the noted converging flow regulation port. One or more signals may be sent to an appropriate drive so as to move the above-noted baffle to a position so as to realize the "derived" or "calculated" size of the spacing between the baffle and the flow regulation port. Any appropriate type of drive could be used in this case. Moreover, these "signal-based" airflow regulation principles may be used with any type of flow regulating structure that is able to move in response to a signal to regulate the size of an airflow passage through which all airflow is directed so as to provide an at least substantially uniform flow rate, regardless of the inhalatory forces being generated by a user of the inhaler (again, so long as they are in excess of at least a certain threshold).

A second family of embodiments of the present invention generally relates to an inhaler with operational testing capabilities in relation to an actuator(s) used by the inhaler to eject or discharge an appropriate substance therefrom. A first aspect of this second family of embodiments is embodied by an inhaler in which a test signal is preferably sent at least to each actuator or actuator group that is currently being utilized by the inhaler (e.g., currently actuatable through the inhaler's controlling logic) to eject or discharge a substance from the inhaler. An "actuator group" is a plurality of ejection actuators that is activated by a single, common signal, and the inhaler may include a plurality of these actuator groups with each of these actuator groups being independently actuatable. The test signal of this first aspect preferably does not result in any discharge of any substance from the inhaler and is therefore preferably different in at least some respect to an actuation signal which does result in a discharge from the inhaler (e.g., transmission of an actuation signal to a "working" ejection actuator does result in a discharge from the inhaler). The response of each ejection actuator or actuator group to the test signal associated with the first aspect is somehow evaluated, for instance to assess its operability.

Various refinements exist of the features noted in relation to the first aspect of the second family of embodiments. Further features may also be incorporated in the first aspect of the second family of embodiments as well. These refinements and additional features may exist individually or in any combination. Evaluation of the response of the ejection actuator(s) or actuator group(s) to the test signal associated with the first aspect may entail evaluating each ejection actuator's or actuator group's electrical performance. Consider the case where each ejection actuator is a resistor which should have a relatively constant resistance (as should any given actuator group) in relation to the ejection signals used by the inhaler. This resistance may be calculated using the relationship of R=V/I, where an electrical signal of a known voltage (V) or current (I) may be transmitted to a particular ejection actuator or actuator group and the other of the voltage (V) or current (I) may be measured. Any change of more than a predetermined amount in the resistance (R) of the ejection actuator or actuator group which is determined in accordance with the test signal associated with the first aspect may be indicative of or equated with some type of failure in relation to the particular ejection actuator or actuator group. In the case of an actuator group, any appropriate standard for defining a "failed condition" may be utilized, including where only a single ejection actuator in the group has failed. However, more typically the first aspect will be implemented to allow a predetermined plurality of ejection actuators within a given actuator group to be in a failed condition before the actuator group is considered to be in a failed condition in accordance with the first aspect. It should be appreciated that other types of actuators may be evaluated through their electrical performance as well, such as actuators which are piezoelectric-based.

One option for implementing the first aspect in relation to an ejection actuator or actuator group which "fails" in terms of the evaluation of its response to the noted test signal would be to disable the ejection actuator or actuator group is some fashion in relation to subsequent dosing events, or to at least provide input to the inhaler's controlling logic as to the existence of those ejection actuators or actuator groups which have "failed" the self-test associated with the first aspect. This is particularly relevant in the case where each ejection actuator or actuator group is independently actuatable and where at least substantially a predetermined amount of material is discharged by each ejection actuator or actuator group in response to a predetermined actuation signal. Disabling an ejection actuator or actuator group means that any such actuator or actuator group would not be available for use in a subsequent delivery operation or "dosing event" by the inhaler. Consider the case where the inhaler is somehow "computer-controlled," such as by including a programmable memory for controlling the operation of the inhaler at least in relation to the manner in which the actuation signal(s) is provided to the ejection actuator(s) of the inhaler. A "dosing event" may entail sending the same actuation signal to each of the ejection actuators or actuator groups a plurality of times over a certain time period (e.g., 8 pulses over 2 seconds), but encompasses any predetermined protocol for delivering one or more actuation signals to one or more ejection actuators or actuator groups. Any disabling of any of the ejection actuators or actuator groups as a result of a failure of the self-test in accordance with the first aspect may be recognized/accounted for by the controlling logic of the inhaler of the first aspect, and further may be used by this controlling logic to modify or adjust the execution of a particular dosing event. One option would be for each individual actuation signal that would have been sent to a "disabled" ejection actuator or actuator group for a particular dosing event, to instead be sent to an ejection actuator(s) or actuator group(s) which "passed" the self-test of the first aspect. This may be done in a variety of ways, such as by adding one or more actuation signals onto the "end" of the initial dosing event (i.e., before having been changed). As such, even though one or more ejection actuators or actuator groups in an inhaler may be inoperable (or rendered totally inoperable by the noted disabling function), the inhaler will still be able to accurately deliver at least substantially the same predetermined amount of discharge for a given dosing event as a result of the first aspect of the second family of embodiments.

Another option which may be implemented in addressing a particular ejection actuator or actuator group that has "failed" in accordance with the first aspect is to "re-activate" any ejection actuators or actuator groups of the inhaler which have been temporarily disabled in relation to the controlling logic used by the inhaler. That is, the inhaler associated with the first aspect may in fact include an excess number of ejection actuators or actuator groups in relation to the number of ejection actuators or actuator groups that are actually desired/needed for the inhaler at any one time. The controlling logic of the inhaler of the first aspect thereby may be "programmed" to only use some of the ejection actuators or actuator groups, and those which are currently not needed may be temporarily disabled (e.g., by the controlling logic being programmed so as to not send an actuation signal to the same during any dosing event). Ejection actuators or actuator groups that have "failed" in accordance with the first aspect and identified as such may be replaced on a one-for-one basis by a corresponding "excess" ejection actuator or actuator group of the inhaler. That is, the controlling logic of the inhaler may be re-programmed to not utilize a certain ejection actuator or actuator group that has "failed" in accordance with the first aspect in favor of one of the excess ejection actuators or actuator groups. Any such "excess" ejection actuators or actuator groups are preferably first tested in relation to their operational abilities before participating in an actual dosing event, including in accordance with the first aspect.

The first aspect may be implemented as part of a testing procedure before distribution of the inhaler for use in respiratory delivery operations. However, preferably the first aspect is implemented so as to at least allow the self-test of the first aspect to be executed after the inhaler has been released for distribution to inhaler users. This may be left up to the discretion of the user by providing for manual initiation of the self-test of the first aspect, or the self-test could be programmed into the controlling logic of the inhaler such that the self-test of the first aspect would be automatically run on some basis. In the latter regard, it may be desirable to execute the self-test of the first aspect before each dosing event to be executed by the inhaler or at least on some type of a periodic basis.

A second aspect of the second family of embodiments extends the above-noted first aspect to monitoring the performance of each ejection actuator or actuator group using the actual actuation signals, namely those signals which do result in a discharge from the inhaler and at least generally in the same manner discussed above in relation to the first aspect and its "test signal." That is, the performance of each ejection actuator or actuator group in the second aspect is monitored/evaluated based upon the actuation signal sent thereto in an actual dosing event, typically in relation to its operational performance.

Various refinements exist of the features noted in relation to the second aspect of the second family of embodiments. Further features may also be incorporated in the second aspect of the second family of embodiments as well. These refinements and additional features may exist individually or in any combination. Initially, and as noted above, the basic principles discussed in relation to the first aspect are equally applicable to the second aspect. There are, however, a number of areas which warrant specific discussion in relation to the second aspect. Any ejection actuator or actuator group which is identified as having failed in relation to the second aspect may be addressed in a number of manners. One way would be to re-send each actuation signal, which was initially sent to a "failed" ejection actuator or actuator group, to another ejection actuator or actuator group which did not "fail" in accordance with the second aspect. This may be difficult to implement on a "real time" base or during a given dosing event. The more likely implementation would be to provide some notification to the user of the inhaler of a "failed" dosing event, and to remedy the failure for the next dosing event in any of the above-described manners (e.g., by using the existing ejection actuators or actuator groups that "passed" the evaluation to receive a number of additional actuation signals equal to the number of actuation signals that were sent to "failed" ejection actuators or actuator groups in the preceding dosing event; by "adding" an "excess" ejection actuator(s) or actuator group(s) into the "active" ejection actuators or actuator groups that are available to the inhaler for a given dosing event so as to replace the failed ejection actuator(s) or actuator group(s)).

Yet another possibility in relation to the foregoing would be to notify the user that a "make-up" dosing event should be executed, as well as possibly the time at which the "make-up" dosing event should be executed. This is possible with the inhaler of the second aspect based upon a number of factors. Having independently actuatable ejection actuators or actuator groups allows for very precise control of the amount of substance that is discharged by the inhaler in a given dosing event. Since there is precise control over the signals and including in relation to the number of signals which are issued, and further since a single actuator or actuator group will dispense a certain amount in response to a certain signal, the amount of substance which is discharged by an inhaler of the second aspect in a given dosing event can be precisely determined. The inhaler of the second aspect will have already determined the particular ejection actuator(s) or actuator group(s) that failed in relation to a given dosing event. In addition, the inhaler of the second aspect may be configured to keep track of how may actuation signals were sent to these ejection actuators or actuator groups in their "failed" condition. Therefore, the inhaler of the second aspect may be configured to define a "make-up" dosing event as a transmission of new actuation signals to one or more ejection actuators or actuator groups which were operational in the immediately preceding dosing event or otherwise operational (e.g., an "excess" actuator"), where these new actuation signals are equal in number to the number of actuation signals that were sent to "failed" ejection actuators or actuators groups in the immediately preceding dosing event in accordance with the second aspect.

A third family of embodiments of the present invention is generally directed to an inhaler that is used to discharge an appropriate substance therefrom for inhalation by a user. A first aspect of the third family of embodiments is embodied by an inhaler that includes a plurality of ejection actuators or groups of ejection actuators. Any such actuator group of multiple actuator groups includes at least one and typically a plurality of ejection actuators that are simultaneously activated by a single, common signal. Preferably each ejection actuator or actuator group is independently actuatable or addressable by what may be characterized as the controlling logic of the inhaler. That is, an actuation signal (or any signal for that matter, such as a self-test signal) may be transmitted to any designated ejection actuator or actuator group. These ejection actuators or actuator groups may be mounted or exist on a common ejection head or the like. Alternatively, the inhaler may include a number of separate ejection heads, each of which includes at least one and more typically a plurality of ejection actuators or actuator groups. In any case, the number of ejection actuators which are currently "active" is less than the total number of ejection actuators which exist for the inhaler. That is, the inhaler does not at any one time utilize all of the ejection actuators for accomplishing a given dosing event. Stated another way, at least some of the ejection actuators that exist for the inhaler are either temporarily or permanently disabled so as to not be able to at least currently discharge a substance from the inhaler.

Various refinements exist of the features noted in relation to the first aspect of the third family of embodiments. Further features may also be incorporated in the first aspect of the third family of embodiments as well. These refinements and additional features may exist individually or in any combination. One way of characterizing the first aspect is as a method for making the above-described inhaler in which more than the desired/required number of ejection actuators is installed for the inhaler. In this case, there could be a testing of at least some, and more preferably all, of the ejection actuators or actuator groups either before or after installation of the same for the inhaler, but nonetheless before release of the inhaler for distribution to users. Assume that the inhaler is designed to have "x" operational ejection actuators or actuator groups. More than "x" ejection actuators or actuator groups are manufactured and installed for the inhaler. Testing of the ejection actuators or actuator groups of the inhaler may be terminated when at least "x" ejection actuators or actuator groups have been determined to be suitably operational. However, preferably all of the ejection actuators or actuator groups are tested for operational capabilities for determining or identifying whether there are any excess operational ejection actuators or actuator groups for other purposes (e.g., for "reactivation" if any of the originally operational ejection actuators or actuator groups subsequently fails and as determined in accordance with a self-test protocol described herein).

The testing of the various ejection actuators or actuator groups may be characterized as determining the operational capabilities of ejection actuators or actuator groups on an individual basis. Testing of the operational capabilities of the individual ejection actuators or actuator groups may be accomplished in any appropriate manner for purposes of the first aspect of the third family of embodiments. For instance, optical testing techniques may be employed to determine if a given ejection actuator or actuator group is producing an appropriate discharge when a representative actuation signal is transmitted to the particular ejection actuator or actuator group (e.g., by optically examining a nozzle through which a particular ejection actuator discharges a substance from the inhaler or nozzles through which a particular group of ejection actuators discharge a substance from the inhaler). Another option would be to evaluate the electrical performance of a particular ejection actuator or actuator group. Electrical performance evaluations need not necessarily utilize an actual actuation or ejection signal, but instead may utilize a test signal which is different from an actuation signal that would be utilized by the inhaler for a given dosing event. For instance, a test signal need not result in any discharge by a particular ejection actuator or actuator group which receives this test signal. Consider the case where each of the various ejection actuators is a resistor which should have a relatively constant resistance in relation to the ejection signals commonly used by the inhaler. This resistance may be calculated using the relationship $R=V/I$, where an electrical signal of a known voltage (V) or current (I) may be transmitted to a particular ejection actuator and the other of the voltage (V) or current (I) may be measured. Any change in resistance (R) of the ejection actuator or actuator group which is determined in accordance with the test signal associated with this variation of the first aspect may be indicative of some type of failure in relation to the particular ejection actuator or actuator group. Other types of actuators may be evaluated through their electrical performance as well, such as actuators which are piezoelectric-based.

One option for implementing the above-noted variation of the first aspect would be to have an ejection actuator or actuator group which "fails" in terms of the evaluation of its response to the noted operational testing either be permanently or temporarily disabled in relation to the controlling logic of the inhaler. This is particularly relevant in the case where each ejection actuator or actuator group is independently actuatable and where a predetermined amount of material is discharged by each ejection actuator or actuator group in response to a predetermined actuation signal. Disabling an ejection actuator or actuator group means that any such actuator or actuator group would not be available for use in a subsequent delivery operation or "dosing event" by the inhaler, at least in the current state of the inhaler control logic. A "dosing event" may entail sending the same actuation signal to a certain number of the ejection actuators or one or more actuator groups a plurality of times over a certain time period (e.g., 8 pulses over 2 seconds), but encompasses any predetermined protocol for delivering one or more actuation signals to one or more ejection actuators or one or more actuator groups. Any disabling of any of the ejection actuators or actuator groups as a result of identifying at least certain inadequacies in relation to its operational capabilities in accordance with the first aspect means that these ejection actuators or actuator groups would not participate in any dosing event based upon the current status of the controlling logic of the inhaler.

Disablement of one or more ejection actuators or one or more actuator groups for a given inhaler may be accomplished in a permanent or temporary manner. Any such disabling of ejection actuators or actuator groups again would take place in accordance with the first aspect only after there was a determination that a predetermined number of ejection actuators or actuator groups were operational for purposes of the inhaler. Permanently disabling one or more ejection actuators or actuator groups possibly may be accomplished by sending a certain signal to the desired ejection actuator(s) or actuator group(s) (e.g., by passing a high current through a resistance-based actuator). This manner of disabling any excess ejection actuators or actuator groups would not require the controlling logic of the inhaler to "know" of the disabled condition of any of its ejection actuators or actuator groups. That is, the controlling logic of the inhaler could still send a signal to each ejection actuator or actuator group that is installed for the inhaler, although the disabled ejection actuators or actuator groups would not respond to any such actuation signal in a manner which would yield a discharge. Another option would be to "program" the controlling logic of the inhaler so as to not send any actuation signal to any "disabled" ejection actuator or actuator group for any dosing event. One advantage of this latter configuration would be to conserve power for the inhaler, particularly if the inhaler was configured as a portable and included an "on-board" power supply.

A fourth family of embodiments of the present invention generally relates to controlling the manner in which an inhaler executes a dosing event where an appropriate substance is ejected or otherwise dispensed from the inhaler. A first aspect of the fourth family of embodiments is generally embodied in an inhaler in which the operational capabilities of at least one and more preferably each ejection actuator or actuator group of the inhaler is at least at sometime determined (e.g., before, during, or after a dosing event). An "actuator group" is a plurality of ejection actuators that may be simultaneously activated by a single or common signal or in some other predetermined manner. The inhaler may include a plurality of these actuator groups, with each of these actuator groups preferably being independently actuatable. One or more parameters that control the execution of a given dosing event for the inhaler (hereafter its associated "dosing event control logic") is at least somehow established or defined by an inhaler in accordance with principles of the first aspect based upon this information on the operational capabilities of at least some of the ejection actuators or actuator groups of the inhaler.

Various refinements exist of the features noted in relation to this first aspect of the fourth family of embodiments. Further features may also be incorporated in the first aspect of the fourth family of embodiments as well. These refinements and additional features may exist individually or in any combination. A "dosing event" may entail sending the same actuation signal to one or more individual ejection actuators, one or more actuator groups, or some combination thereof a plurality of times over a certain time period, but encompasses any predetermined protocol for delivering one or more actuation signals to one or more ejection actuators, one or more actuator groups, or some combination thereof. Typically a pattern of actuation signals will be repeated a plurality of times, and each execution of the pattern may be characterized as a dosing event cycle, dosing event control logic cycle, ejection actuator/actuator group firing cycle, or the like. In some cases, there may be a delay between the time of the last actuation signal in one cycle of a given dosing event and the time of the first actuation signal in the next-in-time cycle of the same dosing event, and this delay may be characterized as "dead time." Dead time may not necessarily exist in all dosing events that are executable by an inhaler in accordance with the fourth family of embodiments.

Each execution of a dosing event by an inhaler in accordance with the fourth family of embodiments ejects or discharges a relatively constant quantity of a given substance (e.g., within an acceptable and relatively small range, or such that there is little to no variation in the total dose delivered in each execution of the same dosing event). A fundamental premise of the dose delivery control that may be incorporated into an inhaler in accordance with the fourth family of embodiments is that a determinable and fixed amount of a given substance will be ejected by a given ejection actuator or actuator group of the inhaler for a given actuation signal. This of course assumes that each ejection actuator or actuator group used in a given dosing event is operational. The determination of the operational capabilities of ejection actuators, actuator groups, or both in accordance with the fourth family of embodiments thereby allows an inhaler in accordance with this fourth family of embodiments to control the execution of a given dosing event in a manner so as to at least improve upon the consistency of the total amount of substance dispensed by an inhaler in each execution of a given dosing event control logic. That is, the inhaler of the fourth family of embodiments may allow for modification of a given dosing event control logic over time so as to at least reduce the variation in the total dose delivered by the inhaler in each execution of this dosing event control logic.

Hereafter the fourth family of embodiments will be discussed in relation to a dosing event control logic that uses only individual ejection actuators. However, the following discussion is equally applicable to any dosing event control logic that uses only actuator groups or some combination of individual ejection actuators and actuator groups.

The fourth family of embodiments may be utilized to modify a dosing event control logic for the next-in-time execution of a dosing event based upon this dosing event control logic. Consider the case where the dosing event control logic at issue and in a first configuration uses a certain number of ejection actuators and where a determination has been made that one or more of these ejection actuators is not operational. The inhaler of the fourth family of embodiments may first determine the number of actuation signals that all non-operational ejection actuators are scheduled to receive in the dosing event control logic in its first configuration, and thereafter may modify the dosing event control logic from its first configuration to a second configuration to instead send these actuation signals to one or more operational ejection actuators that were designated for use by the dosing event control logic in its first configuration. Another option would be to simply identify those ejection actuators that are designated for use by the dosing event control logic in its first configuration and that are not operational, and to modify the dosing event control logic from the first configuration to a second configuration to replace each of these ejection actuators with an ejection actuator that has been determined to be operational and that was not designated for use by the dosing event control logic in its first configuration.

Based upon the foregoing, the inhaler associated with the fourth family of embodiments may in fact include an excess number of ejection actuators in relation to the number of ejection actuators that are utilized by a given dosing event control logic that is available to the inhaler. The dosing event control logic of an inhaler in accordance with the fourth family of embodiments thereby may be "configured" to only use some of the ejection actuators, and those which are currently not utilized by the dosing event control logic in its current form may be temporarily disabled (e.g., by the dosing event control logic being configured so as to not send an actuation signal to the same during the execution of a dosing event based upon this dosing event control logic). Ejection actuators that have been determined to be non-operational in accordance with the fourth family of embodiments and identified as such may be replaced on a one-for-one basis by a corresponding "excess" ejection actuator of the inhaler. That is, the dosing event control logic of an inhaler in accordance with the fourth family of embodiments may be reconfigured so as to not utilize a certain ejection actuator that has been determined to be non-operational in favor of one of the "excess" ejection actuators and in accordance with the fourth family of embodiments. Any such "excess" ejection actuator is preferably first tested in relation to its operational capabilities before being incorporated into the subject dosing event control logic.

Another option for modifying the dosing event control logic for purposes of any subsequent execution of a dosing event in accordance therewith may include retrieving the dosing event control logic in its current form or in a first configuration, and thereafter determining if there are any ejection actuators that are both operational and not currently being utilized by the dosing event control logic in this first configuration. These steps may be executed in any order. There are a number of options for modifying dosing event control logic to a second configuration if there are one or more operational ejection actuators than are not currently being utilized by the dosing event control logic in the first configuration.

One option for modifying the dosing event control logic from its first configuration to a second configuration if there are excess operational ejection actuators in accordance with the fourth family of embodiments would be to incorporate the excess operational ejection actuators into any dead time between adjacent-in-time cycles of the dosing event control logic in its first configuration. This would keep the firing frequency on a per actuator basis the same for a dosing event executed in accordance with the dosing event control logic in its second configuration, but would reduce the overall time required to completely execute such a dosing event since more ejection signals, and thereby more substance, would be delivered in each cycle thereof. Stated another way and for the noted case, additional ejection actuators may be incorporated into each cycle of a dosing event by modifying its associated dosing event control logic without extending the total time required to execute each cycle of the dosing event. It should be appreciated that fewer cycles may be required to complete the execution of a dosing event in accordance with the dosing event control logic in this second configuration, and including only executing part of a cycle to provide the desired total dose for the associated dosing event.

It may not be possible to incorporate all excess operational ejection actuators into each cycle of a dosing event by modifying the dosing event control logic from a first configuration to a second configuration without extending the total time required to execute each cycle of the dosing event (i.e., the firing frequency on a per ejection actuator or actuator group basis may in fact decrease when changing the dosing event control logic from its first configuration to a second configuration). However, the fourth family of embodiments encompasses modifying the dosing event control logic from the first configuration to a second configuration so as to extend each cycle of the dosing event by utilizing at least one additional operational ejection actuators in each cycle. As noted above, fewer cycles may be required to complete the execution of a dosing event in accordance with the dosing event control logic in its second configuration.

The fourth family of embodiments also may be characterized as establishing or defining the dosing event control logic based upon identifying those ejection actuators that are operational. Information that would be needed to define the dosing event control logic in accordance with the fourth family of embodiments in this case would include the total dose that is desired to be delivered in a dosing event executed in accordance with the dosing event control logic that is currently being defined, as well as the dose that is at least assumed to be delivered by each operational ejection actuator on a per actuation signal basis. For instance, a representative number of ejection actuators may be evaluated to determine the amount of substance discharged therefrom based upon a certain predetermined actuation signal. The average discharge from each such ejection actuator may then be utilized by the fourth family of embodiments. In any case, dividing the desired total dose for the subject dosing event by the dose delivered per actuation signal per ejection actuator provides the total number of actuation signals that will be required to be utilized by its corresponding dosing event control logic. Dividing the total number of actuation signals by the total number of operational ejection actuators then determines the number of cycles to be utilized by the dosing event control logic. The firing pattern within each cycle may then be established in any appropriate manner.

The fourth family of embodiments may determine that one or more of the ejection actuators that were designated for use in a given dosing event through its dosing event control logic did not in fact participate in the subject dosing event to the extent required by the subject dosing event control logic (e.g., the operational capabilities of a particular ejection actuator designated for use in a given dosing event may be evaluated during the execution of the dosing event). There are a number of options for dealing with this situation. One way would be to in effect determine the total number of actuation signals that were sent to non-operational ejection actuators during the execution of the subject dosing event in accordance with its dosing event control logic, and to then send this same number of actuation signals to one or more operational ejection actuators. This may be difficult to implement on a "real time" base or during the execution of the subject dosing event in accordance with its dosing event control logic, although such is encompassed by the fourth family of embodiments. The more likely implementation would be to provide some notification to the user of the inhaler of a "failed" dosing event, and to remedy the failure for the next dosing event in any of the above-described manners (e.g., by using the existing ejection actuators that were determined to be operational to receive a number of additional actuation signals equal to the number of actuation signals that were sent to non-operational ejection actuators or actuator groups in the preceding execution of the subject dosing event; by "adding" an "excess" ejection actuator(s) into the "active" ejection actuators that are available to the inhaler for a given dosing event so as to replace the failed ejection actuator(s)).

Yet another possibility in relation to the foregoing would be to notify the user that a "make-up" dosing event should be executed, as well as possibly the time at which the "make-up" dosing event should be executed. This is possible with the inhaler of the fourth family of embodiments based upon a number of factors. Having independently actuatable ejection actuators allows for very precise control of the amount of substance that is discharged by the inhaler in a given dosing event. Since there is precise control over the actuation signals and including in relation to the number of signals that are issued, and further since a single ejection actuator will dispense a certain amount in response to a certain actuation signal, the amount of substance that is discharged by the inhaler of the fourth family of embodiments in a given dosing event can be relatively precisely determined. The inhaler of the fourth family of embodiments will have already determined the particular ejection actuator(s) that failed in relation to the execution of a given dosing event. In addition, the inhaler of the fourth family of embodiments may be configured to keep track of how may actuation signals were sent to these ejection actuators in their "failed" or non-operational condition. Therefore, the inhaler of the fourth family of embodiments may be configured to define a "make-up" dosing event as a transmission of new actuation signals to one or more ejection actuators which were operational in the immediately preceding execution of the subject dosing event or otherwise operational (e.g., an "excess" actuator"), where these new actuation signals are equal in number to the number of actuation signals that were sent to "failed" or non-operational ejection actuators in the immediately preceding dosing event in accordance with the fourth family of embodiments.

DESCRIPTION OF ILLUSTRATED EMBODIMENTS

The present invention will now be described in relation to the accompanying drawings which at least assist in illustrating its various pertinent features. One embodiment of a respiratory delivery system 10 is presented in FIGS. 1–3C, which in the illustrated embodiment is in the form of a portable inhaler 14. The inhaler 14 is portable and orally delivers any type of flowable substance to an individual. Most typically this will be some type of medicament which is stored in liquid form within the inhaler 14. Hereafter, the respiratory delivery system 10 will be described in relation to this medicinal application. However, gaseous substances could also be delivered by the inhaler 14, as well as non-medicinal substances both in liquid or gaseous form, as well as in powder form within a suspension. Moreover, the inhaler 14 could be used for topical or nasal delivery of these types of substances as well.

Two fundamental assemblies define the inhaler 14. One is a handpiece 16 and the other is a cartridge assembly 28. Generally, the handpiece 16 includes certain electronics for controlling the operation of the inhaler 14 and recording information on the use thereof. On the other hand, the cartridge assembly 28 includes a supply of medicament and a "head" of sorts through which medicament is discharged from the inhaler 14 in the form of droplets.

One component of the handpiece 16 for the inhaler 14 is an at least generally cylindrical housing 18. Although the illustrated embodiment is of cylindrical shape throughout the entire extent of the inhaler housing 18, a different shape could be implemented. Discharges from the inhaler 14 are through an end 22 of the housing 18 which defines a discharge outlet. Typically the discharge end 22 of the housing 18 is inserted within the mouth of an individual that is using the inhaler 14. A mouthpiece or the like could be formed on the discharge end 22 of the inhaler 14 if desired as well (not shown). The opposite end of the inhaler housing 18 is identified by the reference numeral 26.

Certain electrical components are preferably utilized by the inhaler 14. Airflow past these electrical components could possibly have an adverse effect on their operation. Therefore, in one embodiment the end 26 of the inhaler housing 18 is closed. Air is instead drawn within the inhaler housing 18, for the introduction of a plurality of droplets therein for inhalation by an individual using the inhaler 14 in a manner which will be discussed in more detail below, through a plurality of air intakes slots 82 which extend through the inhaler housing 18 as shown in FIG. 2 and which each define an inhaler inlet. Generally the noted electrical components are located within the inhaler housing 18 somewhere between the air intake slots 82 and the closed end 26 of the inhaler housing 18 so that airflow is not directed thereby during inhalation by an individual using the inhaler 14. Notwithstanding these potential benefits of the slots 82, one or more air intake orifices could be disposed on the end 26 of the inhaler housing 18 or at other appropriate locations on the inhaler housing 18. In addition, the shape(s) of these slots 82, while illustrated as being rectangular, can be any shape which allows air to flow into the inhaler housing 18.

The cartridge assembly 28 is detachably interconnected with the inhaler housing 18 of the handpiece 16 such that one cartridge assembly 28 may be removed from the inhaler housing 18 by an individual and replaced with a structurally similar cartridge assembly 28. A "snap-lock" interconnection between the cartridge assembly 28 and inhaler housing 18 may be utilized (not shown). An appropriate button or other mechanism may be utilized to remove the cartridge assembly 28 from within the inhaler housing 18 or to disengage the "snap-lock" interconnection. Both insertion and removal of the cartridge assembly 28 may be through the discharge end 22 of the inhaler housing 18, although the inhaler housing 18 could be formed in multiple and detachably interconnected parts as well (e.g., through a threaded interconnection) to provide for installation and removal of the cartridge assembly 28 as well (not shown). In any case, one reason for providing a readily removable cartridge assembly 28 is to allow an individual to use the same inhaler 14 to discharge multiple medications. More than one individual could also use the same inhaler 14 to discharge one or more medications contained in one or more cartridge assemblies 28 possessed by a given individual.

The cartridge assembly 28 includes a medicament container 46 which contains a supply of a certain medicament. Multiple medicament containers 46 could also be utilized by the cartridge assembly 28 to provide for the discharge of medicaments simultaneously or any one medicament dependent on need (not shown). Various types of information regarding this medicament and/or this particular medicament container 46 are stored electronically on a chip 48 which is attached to or integrally formed with the medicament container 46. Information which may be included on the chip 48 includes: 1) the identity of the particular medicament within the medicament container 46; 2) the type of this particular medicament; 3) the concentration of this particular medicament; 4) the total volume of this particular medicament initially included within the medicament container 46 before any discharges to an individual; 5) the identity of the individual designated for use of the medicament stored in the medicament container 46; 6) relevant limitations regarding the use of the medicament stored in the medicament container 46 (e.g., not to be used within a the certain time period of an administration of a different medicament which may be contained in another cartridge assembly 28 and discharged from the same inhaler 14, or so as to reduce the potential for having adverse medicament interactions from multiple dosings using the inhaler 14); 7) a protocol for controlling the discharge of the medicament from the medicament container 46 (e.g., an actuation signal, required time intervals between "dosing events", with each "dosing event" being a single or predetermined number of discharges from the inhaler 14); 8) an access code which must be entered in order for the inhaler 14 to be operational with the particular cartridge assembly 28; and 9) "protocol" regarding how dispensation of medicament and/or the amount thereof should be modified, if at all, based upon patient requirements or otherwise. Data on the use of the cartridge assembly 28 may also be recorded on the chip 48 in an appropriate database structure or the like (e.g., the chip 48 may also include one or more electronic memories). For instance, the time and date of each "dosing event" or each single discharge from the inhaler 14 may be recorded on the chip 48 for future use/evaluation. Moreover, information regarding the operability of any actuators 42 of a droplet ejection device 30 used by the inhaler 14 may also be stored on the chip 48. Information regarding the number and location of any actuators 42 of a droplet ejection device 30 used by the inhaler 14 which have been determined to have "failed" in accordance with either of the protocols discussed in relation to FIGS. 8 and 9 below may also be stored on the chip 48.

Medicament from the medicament container 46 is discharged from the portable inhaler 14 preferably in the form of a plurality droplets which are carried out through the discharge end 22 of the inhaler housing 18 by/during an inhalation stream. In this regard, each cartridge assembly 28 for the inhaler 14 also includes a droplet ejection device 30, which is fluidly interconnected with its corresponding medicament container 46 by an appropriate fluid interconnect 54. Any way of fluidly interconnecting the droplet ejection device 30 and medicament container 46 may be utilized. The droplet ejection device 30 projects at least generally toward the discharge end 22 of the inhaler housing 18 when loaded within the inhaler 14.

Various types of delivery or ejection techniques/componentry may be utilized by the inhaler 14, including those presented in U.S. Pat. No. 5,894,841 to Voges, which issued Apr. 20, 1999, and which is incorporated by reference in its entirety herein. Details of one embodiment of the droplet ejection device 30 are presented in FIGS. 3A–C. The droplet ejection device 30 includes a plurality of droplet ejection assemblies 32. Each droplet ejection assembly 32 includes an actuator 42 which is aligned with and separated from a corresponding discharge orifice(s) 34 by a space 38. Medicament from the medicament container 46 is disposed within this space 38 at least just prior to ejection (e.g., medicament may be continually within the space 38; all or substantially all of the medicament within the space 38 associated with the particular droplet ejection assembly 32 may be discharged on actuation thereof, and thereafter may be replenished after such an actuation). Actuation of the portable inhaler 14 causes each actuator 42 which receives an actuation signal to discharge medicament through its corresponding discharge orifice(s) 34 in the form of one and typically a plurality of droplets. All of the actuators 42 may be activated simultaneously, or the plurality of actuators 42 may be activated in some type of sequence or firing pattern. Preferably each actuator 42 is independently actuatable. Although the illustrated embodiment shows a one-to-one relationship between the actuators 42 and discharge orifices 34, there may be multiple actuators 42 that discharge out of a common discharge orifice 34, or a given actuator 42 may discharge out of multiple discharge orifices 34 (not shown).

In one embodiment, the actuators 42 are resistors and the actuation signal provided thereto affects a rapid increase in the temperature of an actuator 42 which receives such a signal. This rapid increase in the temperature of each "activated" actuator 42 forms/creates a bubble directly adjacent to the actuator 42. Enlargement of this bubble in the direction of its corresponding discharge orifice 34 from the rapid temperature increase displaces that medicament, which is located between the bubble and the corresponding discharge orifice(s) 34, out through the discharge orifice(s) 34.

Activation of any droplet ejection assembly 32 of the droplet ejection device 30 may be accomplished through a controller assembly 62 which is part of the handpiece 16 of the inhaler 14. In this regard, an appropriate operative interconnect 70 extends between and interconnects the droplet ejection device 30 and the controller assembly 62, while another operative interconnect 72 extends between and interconnects the chip 48 of the medicament container 46 and the controller assembly 62. Any way of appropriately operatively interconnecting the controller assembly 62 of the handpiece 16 and the cartridge assembly 28 may be utilized. In fact, the "electronics" or one or more aspects of the control assembly 62 could actually be incorporated into the structure of the droplet ejection device 30. In any case, the controller assembly 62 may include one or more of a microprocessor, a programmable logic control, an electronic memory or memories, and one or more clocks. Generally, the controller assembly 62 is able to read an operating protocol which is stored on the chip 48 of the cartridge assembly 28 and to operate the droplet ejection device 30 of the cartridge assembly 28 in accordance with this protocol (e.g., the number of discharges which define a "dosing event," the lapse of time required between individual discharges, the lapse of time required between dosing events). Various types of data may also be preferably stored on/through the controller assembly 62. For instance, the time and date of each actuation of the inhaler 14 may be recorded/retained for future use/evaluation. Moreover, information for controlling access (e.g., security) to or in relation to the portable inhaler 14 may be stored on/through the controller assembly 62, as may be information relating to controlling the operation of the inhaler 14.

Components of the controller assembly 62 are powered by an "on-board" power supply 74 (e.g., rechargeable battery) which is operatively/electrically interconnected therewith, and which is also part of the handpiece 16. Other components of the inhaler 14 may be electrically interconnected with the power supply 74 as well. Activation of the inhaler 14 may be automated via an appropriate sensor 58 (e.g., airflow, pressure) which is operatively interconnected with the controller assembly 62, and thereby the power supply 74, through the controller assembly 62. The sensor 58 is also part of the handpiece 16. Detection of a certain airflow within the inhaler housing 18 may cause the sensor 58 to send a signal to the controller assembly 62, which in turn may send an actuation signal (e.g., a single pulse or a series of defined pulses) over the operative interconnect 70 to the droplet ejection device 30. Droplets of medicament may then be discharged from the droplet ejection device 30 in the above-noted manner. Manual operation of the inhaler 14 may be provided by including an activation switch 86 of the handpiece 16 on an exterior portion of the inhaler housing 18 and which would be operatively interconnected with the controller assembly 62, and thereby the power supply 74. Activating the switch 86 would then send a signal to the controller assembly 62, which in turn would send an actuation signal (e.g., a single pulse or a series of defined pulses) over the operative interconnect 70 to the droplet ejection device 30. Droplets of flowable substance may then be discharged from the droplet ejection device 30 in the above-noted manner. One or both, sensor 58 and activation switch 86 may be used in the design of the inhaler 14.

Figure 4:
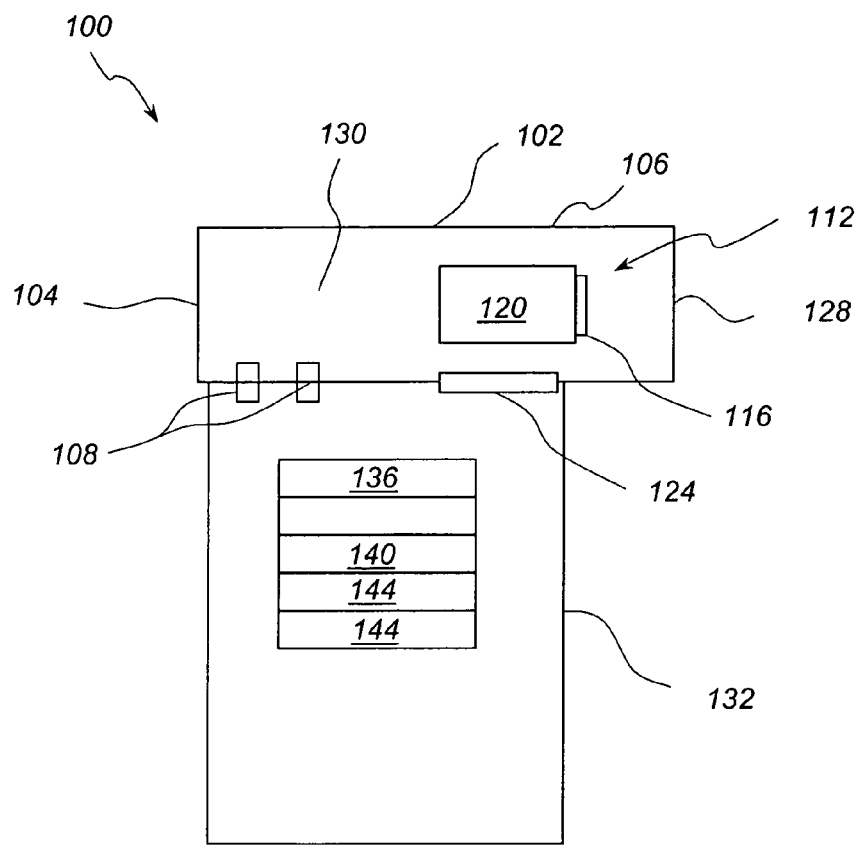
FIG. 4 is a side view of another embodiment of an inhaler.

Another embodiment is presented in FIG. 4 in the form of an inhaler 100. The inhaler 100 generally includes a cartridge/mouthpiece subassembly 102 which is preferably detachably interconnected with a handpiece 132. An appropriate interconnection 124 operatively interconnects the cartridge/mouthpiece subassembly 102 and the handpiece 132 to allow one or more signals (e.g., electrical) to be exchanged therebetween. The cartridge/mouthpiece subassembly 102 generally includes a housing 106 of any appropriate shape and that defines at least one airflow passage 130 therethrough. Air is drawn into the airflow passage 130 through an inlet assembly 104 (e.g., one or more inlet ports) that is disposed at an appropriate location on the housing 106. In the illustrated embodiment, the air inlet assembly 104 is disposed on one end of the cartridge/mouthpiece subassembly 102. The airflow passage 130 directs the airflow to a discharge assembly 128 (e.g., or a mouthpiece) that is also disposed at an appropriate location on the housing 106 as well. In the illustrated embodiment, the discharge assembly 128 is disposed on the opposite end of the cartridge/mouthpiece subassembly 102 in comparison to the inlet assembly 104.

Disposed within the cartridge/mouthpiece subassembly 102 is an ejection assembly 112. Components of the ejection assembly 112 include a head 116 having one or more ejection actuators for ejecting an appropriate substance for inhalation into the airflow that is progressing through the airflow passage(s) 130 in a direction which is at least generally toward the discharge assembly 128. There may be a one-to-one relationship between the ejection actuators and their corresponding discharge orifices, multiple ejection actuators may discharge out of a common discharge orifice, or a given ejection actuator may discharge out of multiple discharge orifices. Any discharge direction from the ejection head 116 may be utilized in relation to the airflow through the airflow passage 130 (e.g., the substance may be directed by the head 116 parallel with the airflow; the substance may be directed by the head 116 perpendicular to the airflow). A supply of the noted substance is stored within a tank 120 of the ejection assembly 112. An appropriate fluid interconnection would therefore exist between the tank 120 and the ejection head 116. A certain quantity of the substance that is being ejected may be stored within the ejection head 116, and replenished via the tank 120. The head 116 could also possibly be configured to eject the substance directly from the tank 120.

The handpiece 132 generally includes electronics or a controller assembly 136 for controlling the operation of the inhaler 100, and including the ejection assembly 112. In one embodiment, the controller assembly 136 is programmable in at least one respect. Other components of the handpiece 132 include an appropriate display 140, a power supply 144 (e.g., a rechargeable battery), and one or more switches 148. The switches 148 may provide for manual activation of the ejection assembly 112, may provide for at least some type of data input, and/or may provide for other user inputs. Initiation of a dosing event by the inhaler 100 also may be accomplished automatically through information received from one or more sensors 108 (e.g., pressure transducers) which monitor the flow rate through the airflow passage 130 (e.g., upon achieving a certain flow rate). These sensors 108 are preferably mounted on the handpiece 132, interface with at least a portion of the airflow through the airflow passage 130, and are operatively interconnected with the controller assembly 136.

There is believed to be some relationship between the flow rate of the airflow through an inhaler and the velocity at which the inhalatory substance is discharged into this airflow for enhancing the efficiency of a given dosing event (e.g., for a more effective delivery of the substance being inhaled to the desired locale). One embodiment for controlling the airflow through an inhaler in a purely mechanical manner (i.e., no need for electronics for controlling/adjusting the airflow, and including no need for an operative interconnection with a controller assembly of any type) is presented in FIG. 5 in the form of an airflow regulation assembly 228. The airflow regulation assembly 228 may be used by any inhaler design, including the inhaler 14 of FIGS. 1–3B and the inhaler 100 of FIG. 4 discussed above.

The inhaler includes airflow conduit 204. Disposed within this airflow conduit 204 is a flow regulation port or throat 208 of the airflow regulation assembly 228 through which substantially all airflow for the inhaler is directed. It may be desirable to position this flow regulation port 208 at least substantially at the inlet to the inhaler, although it could be positioned at some intermediate portion of the inhaler. In any case, the flow regulation port 208 is defined by sidewalls 212 that at least generally converge in the direction of the airflow through the airflow conduit 204, which is represented by the arrow "A." That is, a first end 216 of the inlet port 208 has a larger inner diameter than a second, longitudinally spaced end 220 of the inlet port 208. In the illustrated embodiment, the convergence is linear.

The airflow regulation assembly 228 further includes a baffle 232 that is movably disposed within the flow regulation port 208. The baffle 232 generally includes a head 236 and a shaft 240. The baffle 232 is biased in an upstream direction (opposite the direction depicted by the arrow "A") by an appropriate biasing member 244, such as a coil spring. The coil spring 244 acts on a side of the head 236 of the baffle 232 that is opposite that which interfaces with the air being drawn into the airflow conduit 204 during inhalation by a user of the inhaler. The opposite end of the spring 244 is seated against an appropriate abutment 224 that is appropriately secured to the airflow conduit 204. The abutment 224 is configured to allow for the passage of the airflow therethrough in the direction of the arrow "A", and further may include a guide for movably receiving the shaft 240 of the baffle 232, and further for supporting the baffle 232 within the flow regulation port 208. Any way of supporting the baffle 232 for movement relative to the flow regulation port 208 may be utilized.

Inhalation by a user of an inhaler that utilizes the airflow regulation assembly 228 produces an airflow through the flow regulation port 208 and the airflow conduit 204 that is generally in the direction of the arrow "A." Forces are exerted on the head 236 of the baffle 232 in the direction of the arrow "A" as well by this inhalation. However, the spring 244 opposes these forces. Basically, the size of the head 236 of the baffle 232, the size/contour of the flow regulation port 208, and the biasing forces provided by the spring 244 are selected so as to automatically provide for a desired flow rate through the airflow conduit 204 of the inhaler, regardless of the degree of inhalation generated by the user (if above a certain threshold). Inhalation forces of at least a certain amount will result in at least some compression of the spring 244. Compression of the spring 244 by a movement of the baffle 232 in the direction of the arrow "A" reduces the spacing between the head 236 of the baffle 232 and the inner wall of the flow regulation port 208. Reduction of the spacing between the head 236 of the baffle 232 and the inner wall of the flow regulation port 208 ultimately reduces the flow rate of the airflow passing through the airflow conduit 204. Therefore, there is some relationship between the amount of inhalatory forces that are being generated by a user of an inhaler that includes the airflow regulation assembly 228 and the position of the baffle 232 relative to the flow regulation port 208, which in turn controls the flow rate of the airflow through the inhaler. Generally, above a certain threshold of inhalatory forces, as the inhalation force increases, the size of the spacing between the head 236 of the baffle 232 and the inner wall of the flow regulation port 208 decreases.

Consider the operation of the inlet airflow regulation assembly 228 in relation to three different users which further illustrates the operational principles of the airflow regulation assembly 228. Assume that user A is only able to generate an airflow that generates a force on the head 236 of the baffle 232 that is equal to the biasing forces being exerted on the head 236 by the spring 244. The baffle 232 thereby remains in its "static" position with the largest possible spacing between the head 236 of the baffle 232 and the inner wall of the flow regulation port 208. The flow rate of the airflow through the airflow conduit 204 will then be $F_1$.

Now assume that user B is able to generate a larger inhalatory force than user A. As a result, the baffle 232 will move against the biasing forces being exerted by the spring 244 to reduce the spacing between the head 236 of the baffle 232 and the inner wall of the flow regulation port 208. More specifically, the baffle 232 will move to a position relative to the flow regulation port 204 where the spacing between the head 236 of the baffle 232 and the inner wall of the flow regulation port 208 will at least substantially produce a flow rate through the airflow conduit 204 which is at least substantially equal to $F_1$ (the same flow rate through the airflow conduit 204 realized by user A that in the present example has a reduced inhalatory capacity in relation to user B).

Finally, assume that user C is able to generate a larger inhalatory force than user B. As a result, the baffle 232 will move against the biasing forces being exerted by the spring 244 to further reduce the spacing between the head 236 of the baffle 232 and the inner wall of the flow regulation port 208 in comparison to user B. More specifically, the baffle 232 in the case of user C will move to a position relative to the inlet port 204 where the spacing between the head 236 of the baffle 232 and the inner wall of the flow regulation port 208 will at least substantially produce a flow rate through the airflow conduit 204 which is at least substantially equal to $F_1$ (the same flow rate through the airflow conduit 204 realized by both users A and B, that in the present example have a reduced inhalatory capacity in relation to user C).

Figure 5:
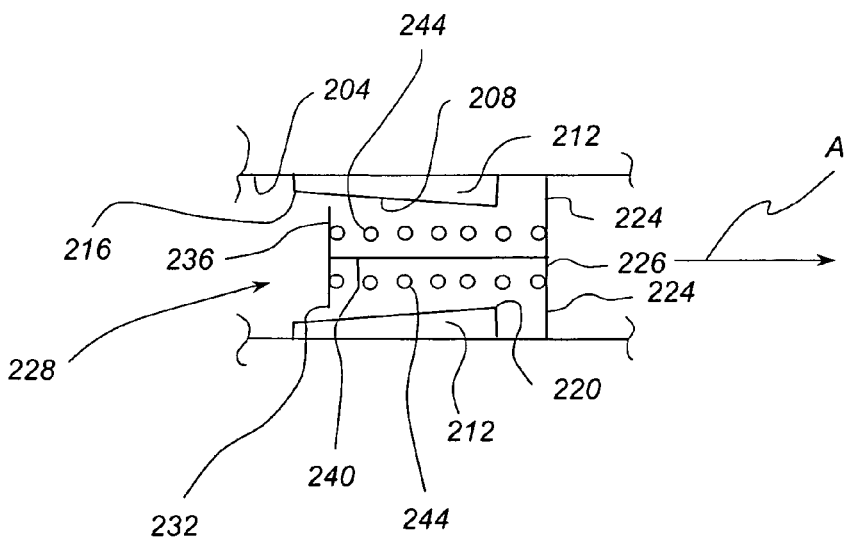
FIG. 5 is a cutaway, side view of one embodiment of an airflow regulation assembly which may be utilized by an inhaler.
Figure 6:
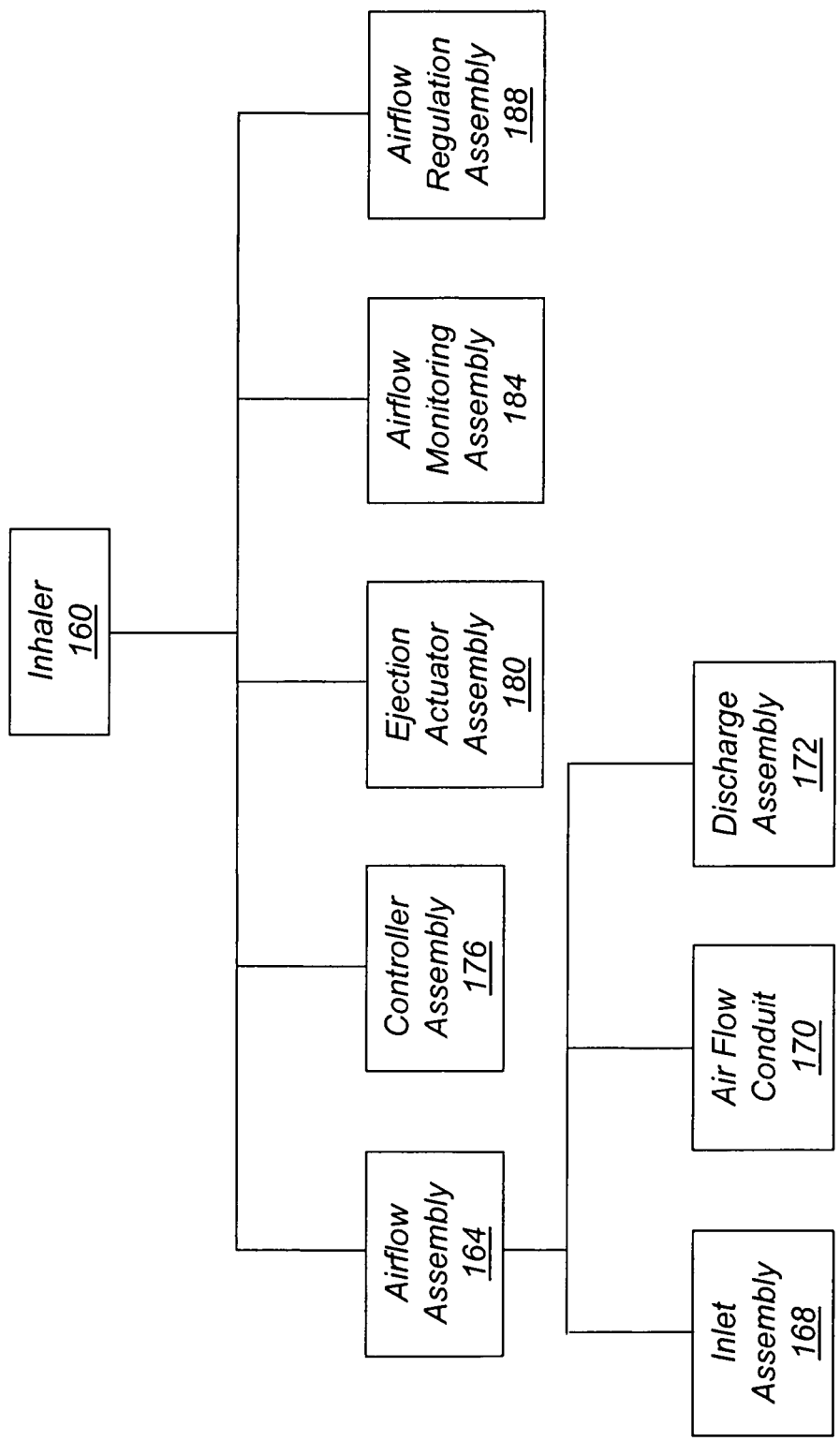
FIG. 6 is a schematic of another embodiment of an inhaler that utilizes an operative interconnection between a controller assembly of the inhaler and an airflow regulation assembly.

The airflow regulation assembly 228 of FIG. 5 is automatically "activated" and "driven" purely by the inhalation forces that are generated by the user. Stated another way, the airflow regulation assembly 228 of FIG. 5 is a purely mechanical system. The principles of the airflow regulation assembly 228 could be implemented in a more elaborate system (e.g., electronic or electromechanical), which will be explained in relation to an inhaler 160 which is schematically presented in FIG. 6. The inhaler 160 generally includes an airflow assembly 164 that in turn includes an inlet assembly 168 (e.g., one or more inlet ports), a discharge assembly 172 (e.g., a mouthpiece, a nasal shroud or mask), and at least one airflow conduit 170 that extends therebetween. Any appropriate substance (e.g., medicament) may be introduced in the airflow being drawn through the airflow assembly 164 by an ejection actuator assembly 180. Any type of ejection actuator design may be utilized by the ejection actuator assembly 180, including those with only a single ejection actuator and those with multiple ejection actuators. Typically the ejection actuator assembly 180 will introduce the desired substance into the airflow somewhere upstream of the discharge assembly 172. Although the ejection actuator assembly 180 may actually be disposed within the airflow conduit 170, the ejection actuator assembly 180 also may be disposed outside of but fluidly interconnected or at least fluidly interconnectable with the airflow conduit 170 for introducing the desired substance into the airflow.

The inhaler 160 also includes a controller assembly 176 for controlling the operation of the inhaler 160 in at least one respect. For instance, the controller assembly 176 may be operatively interconnected with the ejection actuator assembly 180 (e.g., to control the firing sequence of each ejection actuator of the ejection actuator assembly 180 in a given dosing event), although such is not required for purposes of the regulation of the airflow through the inhaler 160. In this regard, the controller assembly 176 of the inhaler 160 is also operatively interconnected with an airflow monitoring assembly 184 and an airflow regulation assembly 188. Generally, the airflow monitoring assembly 184 monitors the airflow through at least a portion of the airflow conduit 204 so as to allow for a determination of the corresponding flow rate. Any appropriate sensor or sensors (e.g., pressure transducers) may be used by the airflow monitoring assembly 184 for this purpose. Determination of the actual flow rate may be accomplished in any manner, including through the controller assembly 176 (e.g., via a microprocessor) based upon input provided by the airflow monitoring assembly 184.

Again, there is believed to be some relationship between the flow rate of the airflow being drawn through the airflow assembly 164 and the velocity at which the desired substance is discharged from the ejection actuator assembly 180 for enhancing the efficiency of a given dosing event. As such, it is believed to be desirable to be above to provide for a certain flow rate through the inhaler 160, which may be realized by adjusting the size of a flow regulation port through which all of the airflow is directed (typically at or close to the inlet). In the case of the inhaler 160, this adjustment is provided through an operative interconnection between the controller assembly 176 and the airflow regulation assembly 188. Generally, the controller assembly 176 sends a signal or set of signals to the airflow regulation assembly 188. This signal moves a flow-regulating portion of the airflow regulation assembly 188 to a certain position to adjust the size of the flow regulation port through which all of the airflow is directed. This adjustment of the size of the flow regulation port provides for a certain, desired flow rate of the airflow through the airflow assembly 164 in the same general manner discussed above in relation to the inlet airflow regulation assembly 228.

Any structure may be utilized by the flow-regulating portion of the airflow regulation assembly 188. For instance, the airflow regulation assembly 188 could utilize the baffle 232 and inlet port 208 utilized by the airflow regulation assembly 228 of FIG. 5. Instead of using inhalation forces to move the baffle 232, the airflow regulation assembly 188 would use some type of device for moving the baffle 232 in a predetermined manner/amount in response to a signal(s) from the controller assembly 176. Moreover, any type of drive that would be appropriate for moving the flow regulating portion of the airflow regulation assembly 188 in an inhaler 160 could be utilized. Finally, any type of flow regulating port could be utilized by the airflow regulation assembly 188. What is of importance in relation to the airflow regulation assembly 188 is that it adjusts the size of an airflow passage through which all airflow passes to maintain the flow rate of the airflow being drawn through the inhaler 160 at least at substantially a constant level regardless of the inhalation forces that are generated by a user (again, assuming that these inhalation forces are above a certain threshold).

Figure 7:
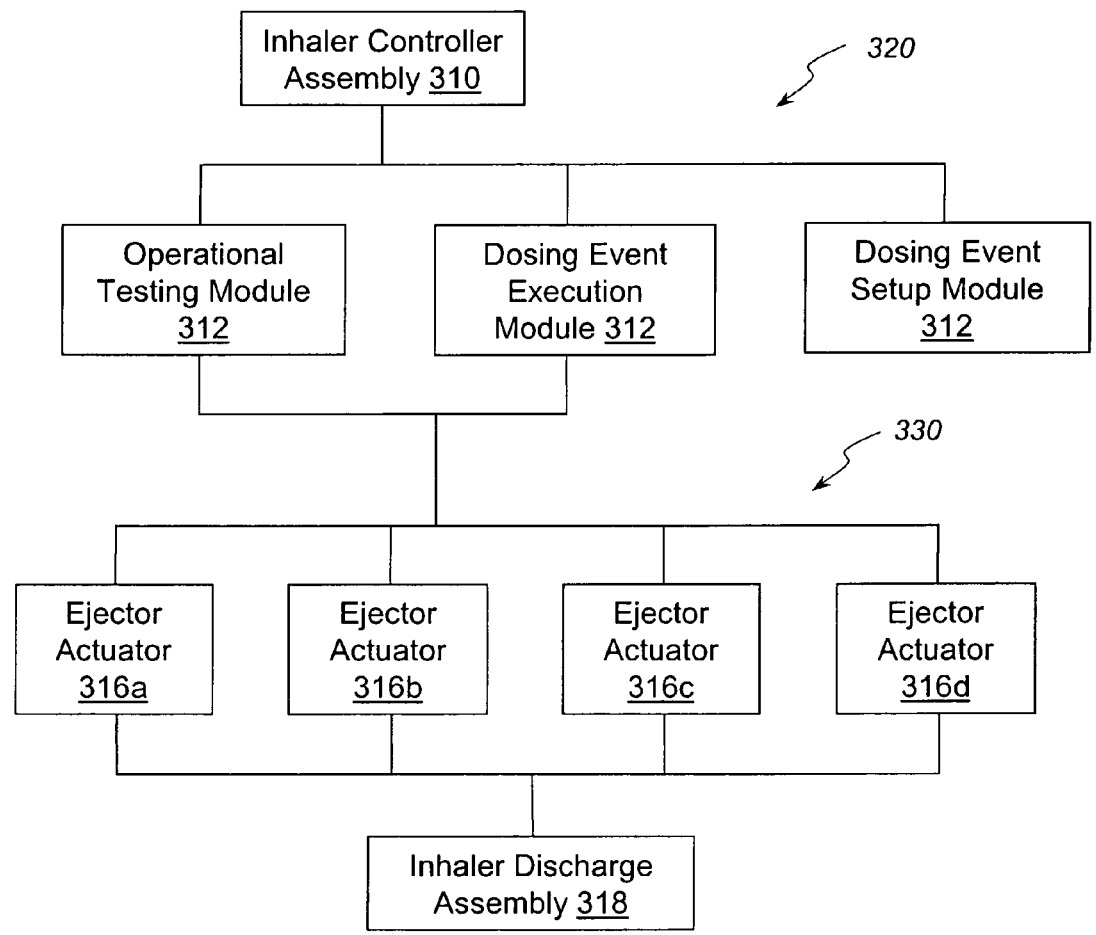
FIG. 7 is a schematic of one embodiment of an inhaler with a controller assembly having both an operational testing module, a dosing event execution module for controlling the provision of one or more signals to a plurality of ejection actuators that are available to the inhaler, and a dosing event setup module for establishing various parameters of a dosing event.

A schematic of another embodiment of a "computer-controlled" inhaler 320 is presented in FIG. 7. The inhaler 320 includes an inhaler controller assembly 310 that controls the operation of the inhaler 320. One component of the inhaler controller assembly 310 is an operational testing module 312. Another component of the inhaler controller assembly 310 is a dosing event execution module 314. Both the operational testing module 312 and a dosing event execution module 314 provide a signal to one or more of the ejection actuators 316 or one or more actuator groups which are utilized by the inhaler 320 to discharge a substance therefrom through an inhaler discharge assembly 318 (e.g., a mouthpiece for oral delivery, a mask for nasal delivery). There may be a one-to-one relationship between the ejection actuators 316 and their corresponding discharge orifice, there may be multiple actuators 316 that discharge out of a common discharge orifice, or a given actuator 316 may discharge out of multiple discharge orifices. Although the inhaler 320 illustrates the use of four ejection actuators 316a–d, any number of ejection actuators 316 may be utilized, including a plurality of groups of ejection actuators 316 with each such group being independently actuatable and with each ejection actuator 316 within a given group being simultaneously activated by a single, common signal. What is of significance in relation to the inhaler 320 is that each of the ejection actuators 316 or actuator groups may be independently actuatable by both the operational testing module 312 and the dosing event execution module 314 of the inhaler controller assembly 310 (e.g., a plurality of ejection actuators 316 may be separated into a plurality of groups, with each group having a plurality of ejection actuators 316, with each of the groups of ejection actuators 316 being independently actuatable by both the operational testing module 312 and the dosing event execution module 314 of the inhaler controller assembly 310, and with each ejection actuator 316 in a given group being simultaneously activated by a single, common signal). It should be appreciated after a review of the following that the operational testing module 312, the dosing event execution module 314, or both could integrated in any number of ways with the inhaler controller assembly 310, and need not necessarily be considered as part thereof.

Generally, the operational testing module 312 of the inhaler 320 of FIG. 7 provides a signal or a series of signals to preferably each of the ejection actuators 316 or to each actuator group to somehow evaluate the performance thereof. In one embodiment, this signal does not result in the discharge of any substance through the inhaler discharge assembly 318, in which case the signal may be characterized as a test signal. However, signals which do result in a discharge may be used by the operational testing module 312 as well, in which case the signal may be characterized as an actuation signal suitable for a dosing event. On the other hand, the dosing event execution module 314 sends an actuation signal or series of actuation signals to one or more of the ejection actuators 316 or to one or more actuator groups in a predetermined manner to provide preferably a predetermined amount of the desired substance through the inhaler discharge assembly 318 ("dosing event"). It should be appreciated that any type of actuator that may be independently actuated may be employed as an ejection actuator 316 (e.g., a resistor-based, piezoelectric-based). Moreover, any way of incorporating the functionality of the operational testing module 312 and the dosing event execution module 314 may be utilized by the inhaler controller assembly 310.

Typically the inhaler 320 will include a rather significant number of ejection actuators 316. In one embodiment, the inhaler 320 includes at least 10 independently actuatable ejection actuators 316 or actuator groups. Not all of the ejection actuators 316 or actuator groups will necessarily be available for use by the inhaler 320 for a given dosing event. One reason for having excess ejection actuators 316 or actuator groups for the inhaler 320 is to increase the yield associated with the production of ejection actuators 316 for the inhaler 320. Typically a plurality of ejection actuators 316 or actuator groups will be mounted upon a common structure and will define an ejection head 330 as illustrated in FIG. 7. Only one ejection head 330 is identified for the inhaler 320 presented in FIG. 7. Multiple ejection heads 330 mounted upon a common structure could be implemented for the inhaler 320 as well. In any case, incorporating more than the required number of ejection actuators 316 into the design of the inhaler 320 means that all of the ejection actuators 316 (or actuator groups) on a given ejection head 330 need not be operational in order for the ejection head 330 to be able to available for use in the inhaler 320.

Figure 8:
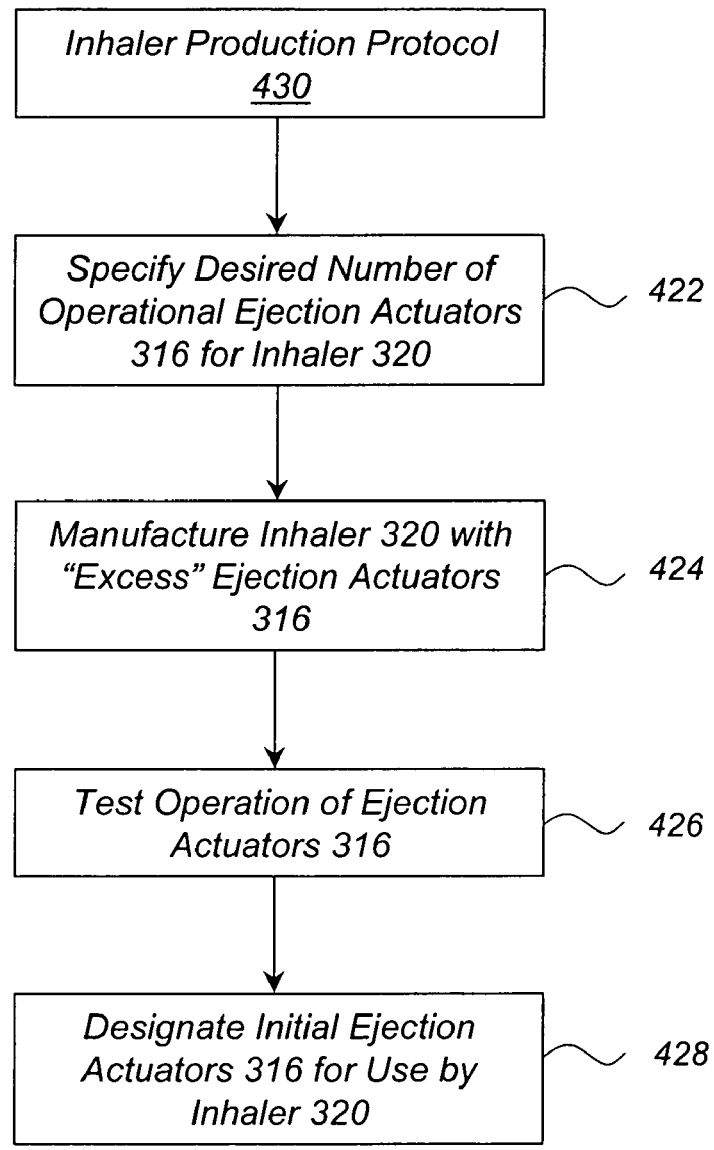
FIG. 8 is one embodiment of a production protocol for the inhaler of FIG. 7.

One embodiment of a method for manufacturing the inhaler 320 with excess ejection actuators 316 or actuator groups is presented in FIG. 8 in the form of an inhaler production protocol 430. The protocol 430 initiates with a step 422 in which the desired number of operational ejection actuators 316 or actuator groups for the inhaler 320 are specified or at least the minimum number of operational ejection actuators 316 or actuator groups for the inhaler 320. Step 424 of the protocol 430 indicates that more than the desired/minimum number of operational ejection actuators 316 or actuator groups are actually manufactured for inclusion in the inhaler 320. This will typically be in the form of manufacturing an ejection head 330 for the inhaler 320 such that the total number of ejection actuators 316 or actuator groups included within the inhaler 320 (whether on one or more ejection heads 330) will be more than desired/required amount set forth in step 422 of the protocol 430. Consider an example where the desired number of operational ejection actuators 316 is 90 and where a single ejection head 330 may be manufactured so as to include 100 of these ejection actuators 316. Although only 90 ejection actuators 316 are desired/required for use in the inhaler 320, the ejection head 330 with the 100 ejection actuators 316 thereon is nonetheless installed in the inhaler 320.

Either before or after a given ejection head 330 is physically installed in the inhaler 320, the operation of at least some (more preferably all) of its ejection actuators 316 or actuator groups are tested as set forth in step 426 of the production protocol 430. Any appropriate way for testing the operational capabilities of the various ejection actuators 316 or actuator groups may be utilized. One way to evaluate the operational capabilities of a given ejection actuator 316 or actuator group is through its electrical performance. Consider the case where the ejection actuators 316 are resistors of the type discussed above in relation to the inhaler 14 of FIGS. 1–3C. Any signal which somehow evaluates the electrical performance of the actuators 316 or actuator groups in this case may be utilized by the protocol 430 in its step 426. One alternative would be to send an electrical signal to each of the resistor-based ejection actuators 316 or actuator groups to determine if the resistance of any of the resistor-based ejection actuators 316 or actuator groups has changed from a previously known value (e.g., using the principles of V=IR). Any change in resistance of more than a certain predetermined amount could be associated with the execution of step 426 of the protocol 430. There may be other ways to evaluate the electrical performance of an ejection actuator 316 or actuator group, including when the ejection actuators 316 or actuator groups are other than resistance-based (e.g., piezoelectric-based), as well as other ways to evaluate the performance of the actuators 316 or actuator groups in general and which is within the scope of step 426 of the protocol 430. Another option for evaluating the performance of the ejection actuators 316 or actuator groups would be to utilize optical testing techniques to determine if, upon application of an actuation signal to a given ejection actuator 316 or actuator group, there was in fact a discharge from the inhaler 320 from this particular ejection actuator 316 or actuator group (e.g., to determine if there was a discharge through a nozzle associated with a particular ejection actuator 316 or through nozzles associated with a particular actuator group).

All of the ejection actuators 316 or actuator groups incorporated within the structure of the inhaler 320 need not be tested through execution of step 426 of the protocol 430. For instance, the testing of the ejection actuators 316 or actuator groups included or to be included within a given inhaler 320 through execution of step 426 of the inhaler production protocol 430 may be terminated when at least the number of ejection actuators 316 or actuator groups specified in step 422 of the protocol 430 have "passed" the testing associated with step 426 of the protocol 430. However, more preferably all of the ejection actuators 316 or actuator groups on each ejection head 330 to be installed or which are initially installed in an inhaler 320 are in fact tested through execution of step 426 of the protocol 430 for reasons discussed below in relation to the ejection actuator operational testing protocol 500 of FIG. 9.

The production protocol 430 of FIG. 8 concludes with step 428 which is directed to designating those ejection actuators 316 or actuator groups which are at least initially to be made available for use by the inhaler 320 in which such actuators 316 or actuator groups are installed. There are various ways in which this "designation" may be implemented. For instance, the excess ejection actuators 316 actuator groups may be permanently disabled (i.e., those operational ejection actuators 316 or actuator groups that are in excess of those operational ejection actuators 316 or actuator groups specified in step 422). Application of an "excessive" electrical signal (e.g., at a higher voltage or current than a typical actuation signal for accomplishing a discharge from the inhaler 320) may render the ejection actuator 316 or actuator groups permanently inoperable. This is possible since each of the ejection actuators 316 or actuator groups are preferably independently actuatable. Another option is to simply program the inhaler controller assembly 310 to only use certain of the ejection actuators 316 or actuator groups for any dosing event. One benefit of this strategy is that if one or more of the "active" ejection actuators 316 or actuator groups fail at some point in time during the life of the inhaler 320, any one of the excess ejection actuators 316 or actuator groups which passed the test associated with step 426 of the protocol 430 may be "activated" for purposes of the inhaler controller assembly 310 through the operational testing module 312.

Figure 9:
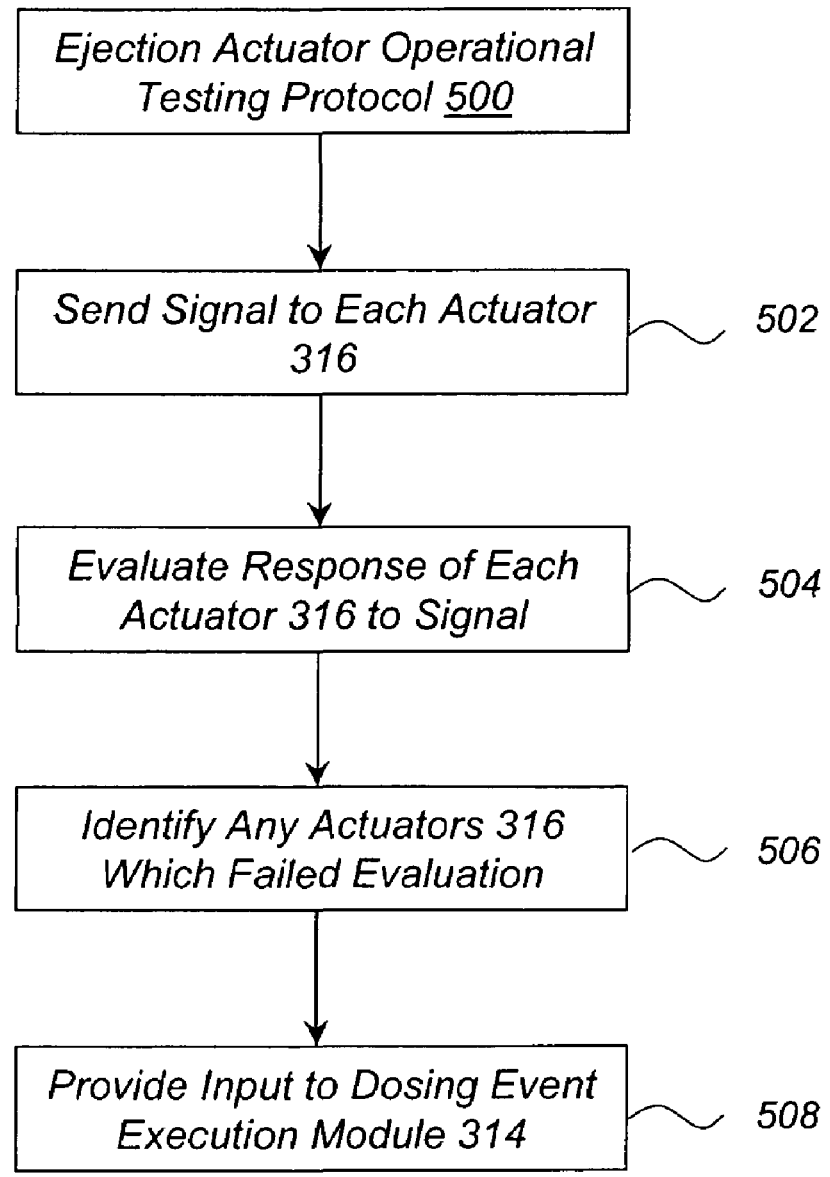
FIG. 9 is one embodiment of an inhaler actuator operational testing protocol that may be used by the operational testing module of the inhaler of FIG. 7.

One embodiment of an inhaler actuator operational testing protocol 500 that may be utilized by the operational testing module 312 is presented in FIG. 9. The protocol 500 is appropriate for any inhaler design which utilizes at least one and more preferably multiple and independently actuatable devices or groups of devices (with each device within a given group being simultaneously activated by a single, common signal) for discharging any substance (e.g., a plurality of droplets) from the associated inhaler. Therefore, the protocol 500 could be utilized by the above-discussed respiratory delivery system 10 of FIG. 1 which again utilizes a plurality of independently actuatable resistors 42. However, the protocol 500 could also be used by an inhaler which utilizes a plurality of independently actuatable piezoelectric-based inhaler ejection actuators.

The operational testing protocol 500 of FIG. 9 will be described in relation to the inhaler 320 of FIG. 7. The protocol 500 includes a step 502 in which a signal is sent by/through the operational testing module 312 to at least each ejection actuator 316 or actuator group of the inhaler 320 that is currently "active" in relation to the inhaler controller assembly 310 (i.e., available for participation in a dosing event as controlled by the inhaler controller assembly 310). All of the ejection actuators 316 or actuator groups that are installed in the inhaler 320 could be tested as well. Typically this will be limited to where the signal is a test signal that does not result in a discharge from the inhaler 320 so as to not modify the desired dosing. In any case, the response of each such ejection actuator 316 or actuator group to its corresponding signal is evaluated by/through execution of step 504 of the protocol 500. Any ejection actuator 316 or actuator group which fails the test is identified in some manner through execution of step 506 of the protocol 500. Input from the operational testing module 312 regarding any "failed" ejection actuators 316 or actuator group is then provided to the dosing event execution module 314 through execution of step 508 of the protocol 500.

Any signal that is appropriate for evaluating the performance of a given ejection actuator 316 or actuator group may be utilized by step 502 of the inhaler ejection actuator operational testing protocol 500 of FIG. 9. One way to evaluate the performance of a given ejection actuator 316 or actuator group is through its electrical performance. Consider the case where the ejection actuators 316 or actuator groups are resistors of the type discussed above in relation to the inhaler 14 of FIGS. 1–3C. Any signal which somehow evaluates the electrical performance of the actuators 316 or actuator groups in this case may be utilized by the protocol 500. One alternative would be to send an electrical signal to each of the resistor-based ejection actuators 316 or actuator groups to determine if the resistance of any of the resistor-based ejection actuators 316 or actuator groups has changed from a previously known value (e.g., using the relationship of R=V/I). Any change in resistance of more than a certain predetermined amount could be associated with a "failure" of the evaluation in the execution of step 506 of the protocol 500. There may be other ways to evaluate the electrical performance of an ejection actuator 316 or actuator group, including when the ejection actuators 316 or actuator groups are other than resistance-based (e.g., piezoelectric-based), as well as other ways to evaluate the performance of the actuators 316 or actuator groups in general and which is within the scope of step 504 of the protocol 500.

Identification of any ejection actuators 316 or actuator groups that have "failed" in relation to the signal that is issued through execution of step 502 of the operational testing protocol 500 of FIG. 9 may be utilized to disable any further operation of the "failed" actuator 316 or actuator group. That is, the input provided by the operational testing module 312 to the dosing event execution module 314 through execution of step 508 of the protocol 500 may result in the dosing event execution module 314 discontinuing any further use of any "failed" actuator 316 or actuator group (i.e., actuation signals for accomplishing a discharge in a dosing event will no longer be sent to a "failed" ejection actuator 316 or actuator group by the dosing event execution module 314 once identified through execution of steps 502–506 of the protocol 500). At a minimum, preferably the dosing event execution module 314 will account for each ejection actuator 316 or actuator group which was identified as "failing" through execution of steps 502–506 of the protocol 500 in subsequent dosing events that are initiated/controlled through the dosing event execution module 314.

There are various ways in which the dosing event execution module 314 may account for input that is provided by the operations testing protocol 500 of FIG. 9. Consider the case where the signal of step 502 of the protocol 500 is a test signal that does not result in any discharge from the inhaler 320. One option would be to "program" the inhaler controller assembly 310 to send an actuation signal that would have been sent to a "failed" ejection actuator 316 or actuator group for a given dosing event, instead to an ejection actuator 316 or actuator group which "passed" the evaluation contemplated by steps 502–506 of the protocol 500 of FIG. 9 for all subsequent dosing events initiated/controlled through the dosing event execution module 314. Another option would be to "activate" one of the excess ejection actuators 316 or actuator groups from the inhaler production protocol 430 of FIG. 8 for each ejection actuator 316 or actuator group, respectively, which failed the operational testing protocol 500 of FIG. 9. This is one reason why it may not be desirable to permanently deactivate or disable ejection actuators 316 or actuator groups which are in excess of the quantity specified in step 422 of the inhaler production protocol 430 of FIG. 8.

Now consider the case where the signal of step 502 of the operational testing protocol 500 of FIG. 9 is an actual actuation signal which is at least intended to result in a discharge from the inhaler 320. There are a number of ways in which the dosing event execution module 314 may account for the identification of any failed ejection actuators 316 or actuator groups in this case as a result of the input provided by step 508. One way would be for the dosing event execution module 314 to re-send each actuation signal, which was initially sent to a "failed" ejection actuator 316 or actuator group, to another ejection actuator 316 or actuator group which did not "fail" in accordance with the execution of steps 502–506 of the protocol 500. This may be difficult to implement on a "real time" base or during a given dosing event. That is, it may be difficult to identify a "failed" ejection actuator 316 or actuator group during an actual dosing event, determine how to account for this failure in the same dosing event, and to accomplish an "additional" discharge which accounts for this failure before expiration of the subject dosing event. The more likely implementation would be for the inhaler 320 to provide some notification to the user of the inhaler 320 of a "failed" dosing event, and to remedy the failure for the next dosing event in any of the above-described manners (e.g., by using the existing ejection actuators 316 or actuator groups that "passed" the evaluation of step 504 to receive a number of additional actuation signals equal to the number of actuation signals that were sent to "failed" ejection actuators 316 or actuator groups in the preceding dosing event; by "adding" an "excess" ejection actuator(s) 316 or actuator group(s) into the "active" ejection actuators 316 or actuator groups that are available to the inhaler 320 for a given dosing event so as to replace the failed ejection actuator(s) 316 or actuator group(s)).

Yet another possibility in relation to how the dosing event execution module 314 may account for the input that is the subject of step 508 of the protocol 500 of FIG. 9 would be to notify the user that a "make-up" dosing event should be executed, as well as possibly the time at which the "make-up" dosing event should be executed. This is possible with the inhaler 320 based upon a number of factors. Having independently actuatable ejection actuators 316 or actuator groups allows for very precise control of the amount of substance that is discharged by the inhaler 320 in a given dosing event. Since there is precise control over the actuation signals and including in relation to the number of actuation signals which are issued, and further since a single actuator 316 or actuator group will dispense a certain amount in response to a certain actuation signal, the amount of substance which is discharged by an inhaler 320 in a given dosing event can be precisely determined. The inhaler 320 will have already determined the particular ejection actuator(s) 316 or actuator group(s) that failed in relation to a given dosing event through execution of steps 502 and 504 of the protocol 500. In addition, the controller assembly 310 of the inhaler 320 may be configured to keep track of how may actuation signals were sent to these ejection actuators 316 or actuator groups in their "failed" condition. Therefore, the inhaler 320 may be configured to define a "make-up" dosing event as a transmission of new actuation signals to one or more ejection actuators 316 or actuator groups which were operational in the immediately preceding dosing event or are otherwise operational (e.g., an "excess" actuator(s) 316), where these new actuation signals are equal in number to the number of actuation signals that were sent to "failed" ejection actuators 316 or actuators groups in the immediately preceding dosing event and as determined in accordance with steps 502 and 504.

The ejection actuator operational testing protocol 500 of FIG. 9 may be implemented as part of a testing procedure before distribution of the inhaler 320 for use in respiratory delivery operations. However, preferably the protocol 500 is implemented so as to allow for the execution thereof at one or more times after the inhaler 320 has been released for distribution to inhaler users. In the case where the signal of step 502 of the protocol 500 of FIG. 9 is a test signal, execution of the protocol 500 may be left up to the to discretion of the user by providing for manual initiation of operational testing protocol 500. Another option would be to have the operational testing protocol 500 be automatically executed on some predetermined basis. For instance, it may be desirable to execute the operational testing protocol 500 before the execution of each dosing event that is initiated/ controlled by the dosing event execution module 314. It also may be desirable to execute the operational testing protocol 500 on some periodic basis.

In the case of both the production protocol 430 of FIG. 8 and the operational testing protocol 500 of FIG. 9, any appropriate standard for defining a "failed condition" in relation to an actuator group may be utilized, including where only a single ejection actuator in the group has failed. However, more typically both the production protocol 430 and the operational testing protocol 500 will be implemented to allow a predetermined plurality of ejection actuators within a given actuator group to be in a failed condition before the actuator group is considered to be in a failed condition in accordance with either of these protocols 430, 500.

Figure 10:
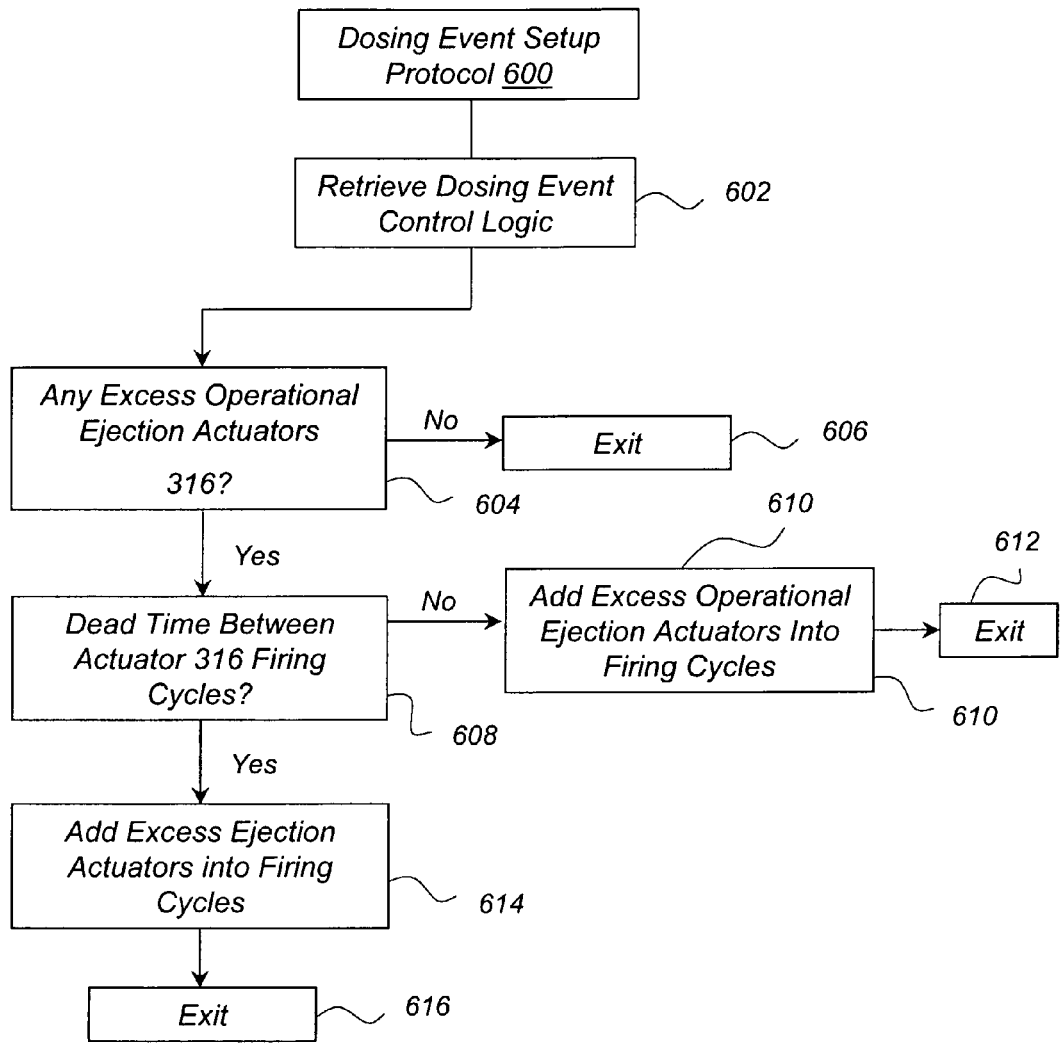
FIG. 10 is one embodiment of a dosing event setup protocol that may be used by the dosing event setup module of the inhaler of FIG. 7.

The above-noted ways in which the dosing event execution module 314 may account for the input that is the subject of step 508 of the protocol 500 of FIG. 9 may be provided through the dosing event setup module 328 of the inhaler 320 of FIG. 7. Generally, the dosing event setup module 328 may be viewed as providing electronic dose delivery control capabilities for the inhaler 320 of FIG. 7. Electronic dose delivery control options other than those discussed above may be utilized through the dosing event setup module 328 as well. Consider the dosing event setup protocol 600 that is presented in FIG. 10 and that may be utilized by the dosing event setup module 328 of the inhaler 320 of FIG. 7. The dosing event setup protocol 600 includes a step 602 in which a dosing event control logic is retrieved. It should be appreciated that multiple dosing event control logic may be available to the dosing event execution module 314 of the inhaler 320 of FIG. 7, in which case the protocol 600 would include any appropriate step(s) or way to retrieve the desired dosing event control logic.

The dosing event control logic that is retrieved in step 602 of the protocol 600 may include identifying which particular ejection actuators 316 or actuator groups are currently designated for use by the dosing event control logic or when in a first configuration, the number of actuation signals that are currently designated to be sent to each of these ejection actuators 316 or actuator groups in this first configuration, and the manner in which these actuation signals are sent to these ejection actuators 316 or actuator groups in this first configuration (e.g., the frequency of the actuation signals on a per ejection actuator 316 or actuator group basis). A pattern or set of actuation signals will be repeated a plurality of times in a dosing event in accordance with its associated dosing event control logic, and each such repetition may be characterized as a "cycle." Each ejection actuator 316 or actuator group that is utilized by a given dosing event logic receives the same number of actuation signals in any given complete cycle as all other ejection actuators 316 or actuator groups that are utilized by this same dosing event logic in the same complete cycle. In one embodiment, there is only one actuation signal per ejection actuator 316 or actuator group per cycle, although this need not necessarily be the case. Consider the case where there are 200 ejection actuators 316 that are currently designated for use by a given dosing event control logic. A "cycle" may include sending the same actuation signal sequentially to each of these 200 ejection actuators 316. Therefore, the time between when an actuation signal is sent to the 1$^{st}$ ejection actuator 316 and the 200$^{th}$ ejection actuator 316 would constitute one cycle. It should be appreciated that the same actuation signal could be sequentially sent to groups of ejection actuators 316, such that the time between when an actuation signal was sent to the first group of ejection actuators 316 and the last group of ejection actuators 316 would also constitute one cycle. In fact, any combination of actuation signals to one or more individual ejection actuators 316, to one or more groups of ejection actuators 316, or both, may constitute a cycle in a given dosing event control logic.

The inhaler 320 may have more ejection actuators 316 or actuator groups than are currently being utilized by the dosing event control logic associated with step 602. That is, the dosing event control logic associated with step 602 may utilized only a certain, limited number of ejection actuators 316 or actuator groups for the execution of a dosing event. Step 604 of the protocol 600 determines if there are more operational ejection actuators 316 or actuator groups for the inhaler 320 than are currently being utilized by the dosing event control logic associated with step 602. One way in which this may be done is through execution of the operational testing protocol 500 of FIG. 9. If the number of operational ejection actuators 316 or actuator groups for the inhaler 320 is equal to or less than the number of ejection actuators 316 or actuator groups designated for use by the dosing event control logic associated with step 602, the protocol 600 proceeds from step 604 to step 606. Step 606 simply provides an exiting function for the protocol 600.

The dosing event setup protocol 600 proceeds from step 604 to step 608 if there are more operational ejection actuators 316 or actuator groups than are currently being utilized by the dosing event control logic associated with step 602. Step 608 is directed to "dead time." There may be a delay between the time that an actuation signal is sent to the last ejection actuator 316 or actuator group in one cycle, and the time that an actuation signal is sent to the first ejection actuator 316 or actuator group in the next-in-time cycle of the dosing event control logic associated with step 602. This may be characterized as "dead time." Dead time may be required in order to allow an ejection actuator 316 or actuator group in the execution of a dosing event in accordance with the dosing event control logic associated with step 602 to be completely "recharged" for the next actuation signal cycle. There may be other reasons for having dead time between adjacent-in-time cycles of a dosing event as well. In any case, step 608 of the dosing event setup protocol 600 inquiries as to whether there is any dead time between adjacent-in-time cycles of the dosing event logic associated with step 602.

The dosing event setup protocol 600 executes step 614 if there is dead time between adjacent-in-time cycles of the dosing event control logic associated with step 602 and provides for adding at least some of the excess ejection actuators 316 or actuator groups into this dead time. This then modifies the dosing event control logic associated with step 602. There may be a limit to the actual number of excess ejection actuators 316 or actuator groups that may be added into the dead time without changing the frequency at which a given ejection actuator 316 or actuator group receives an actuation signal in the execution of a dosing event. For instance, it is possible that there may be a maximum number of ejection actuators 316 or actuator groups that can be simultaneously activated in a given cycle of a dosing event. Therefore and for cases when it is desirable to retain the current cycle time and thereby the ejection actuator 316 or actuator group firing frequency, it may be possible that only a limited number of the excess ejection actuators 316 or actuator groups associated with step 604 will be able to be added to the dosing event control logic associated with step 602 to modify the same. However, the total execution time for the dosing event control logic associated with step 602 will thereafter be reduced when the dosing event control logic associated with step 602 is modified in this manner. That is, each execution of a dosing event in accordance with the dosing event control logic associated with step 602 delivers at least relatively the same total dose (i.e., within preferably a relatively small range such that there is relatively little variation from dosing event to dosing event). Each ejection actuator 316 or actuator group delivers a certain, determinable amount of a desired substance for a given actuation signal. The total number of actuation signals required to deliver the desired total dose for a dosing event associated with the dosing event control logic associated with step 602 then may be derived by dividing the desired total dose for the dosing event by the dose delivered by an ejection actuator 316 or actuator group per actuation signal. Since more actuation signals are being sent to ejection actuators 316 or actuator groups per cycle, the modification of the dosing event control logic associated with step 602 in the above-noted manner will require fewer cycles (including fractions of a cycle).

When there is dead time and when all of the excess ejection actuators 316 or actuator groups cannot be added into the dosing event control logic associated with step 602 without extending the time for each of its cycles, the logic of step 614 may nonetheless provide that that the dosing event control logic associated with step 602 will be modified by adding all of the excess ejection actuators 316 or actuator groups into each of its cycles. This may decrease the ejection actuator 316 or actuator group firing frequency for the now modified current dosing event control logic associated with step 602 in that there would be more of a delay between actuation signals provided to a given ejection actuator 316 or actuator group between adjacent-in-time cycles. However, the total time of the dosing event should be reduced since there will be more actuation signals being provided per cycle in accordance with the foregoing, and thereby less firing cycles overall as well.

Now consider the case where there is no dead time between actuator firing cycles in the dosing event control logic associated with step 602. In this case, the dosing event setup protocol 600 of FIG. 10 executes a step 610. Step 610 provides that at least some of the excess operational ejection actuators 316 or actuator groups be added into the firing cycles of the dosing event control logic associated with step 602. There again may be a limit to the actual number of excess ejection actuators 316 or actuator groups that may be added into a given firing cycle without changing the frequency at which a given ejection actuator 316 or actuator group receives an ejection signal throughout a dosing event. For instance, it is possible that there may be a maximum number of ejection actuators 316 or actuator groups that can be simultaneously activated in a given cycle. Therefore and for cases when it is desirable to retain the current cycle time and thereby the ejection actuator 316 or actuator group firing frequency, it may be possible that only a limited number of the excess ejection actuators 316 or actuator groups will be added to the dosing event control logic associated with step 602 to modify the same. However, the total execution time for a dosing event in accordance with this now modified dosing event control logic would be reduced in this case and in accordance with the foregoing.

When there is no dead time and when all of the excess ejection actuators 316 or actuator groups cannot be incorporated into the dosing event control logic associated with step 602 without extending the time for each of its cycles, the logic of step 610 of the protocol 600 nonetheless may provide that all of the excess ejection actuators 316 or actuator groups will be incorporated into each cycle of the dosing event control logic associated with step 602. This may decrease the ejection actuator 316 or actuator group firing frequency for the now modified dosing event control logic associated with step 602 in that there would be more of a delay between actuation signals provided to a given ejection actuator 316 or actuator group in adjacent-in-time cycles. However, the total time of the dosing event would be reduced since there will be more actuation signals being provided per cycle in accordance with the foregoing, and thereby less firing cycles overall.

Figure 11:
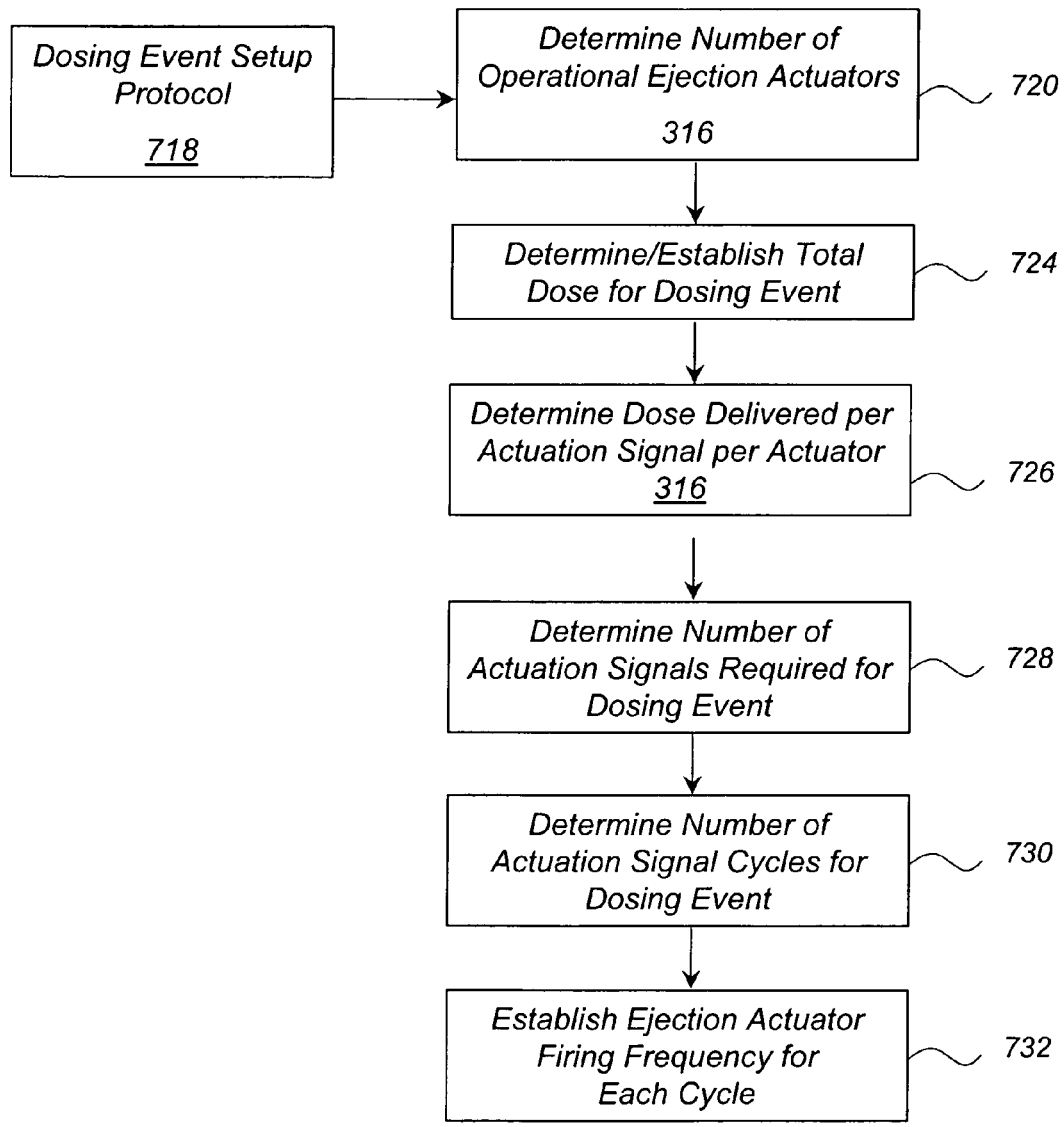
FIG. 11 is another embodiment of a dosing event setup protocol that may be used by the dosing event setup module of the inhaler of FIG. 7.

Another protocol that may be utilized by the dosing event setup module 328 of the inhaler 320 of FIG. 7 is illustrated in FIG. 11 in the form of a dosing event setup protocol 718. Generally, the protocol 718 may be viewed as establishing the dosing event control logic for a given the dosing event. Steps 720, 724, and 726 of the protocol 718 are preparatory in nature and may be executed in any order. Execution of step 720 of the protocol 718 determines the number of ejection actuators 316 or actuator groups of the inhaler 320 that are currently operational. One way in which this may be done is through execution of the operational testing protocol 500 of FIG. 9. Execution of step 724 of the protocol 718 determines the total desired/required dose for the dosing event whose dosing event control logic is currently being defined. Typically this information will be specified by an attending physician or the like and nonetheless may be input to the inhaler 320 in any appropriate manner. Execution of step 726 of the dosing event setup protocol 718 determines the amount of the substance that is at least assumed to be delivered per actuation signal per ejection actuator 316 or group of actuators 316. One way in which this may be done is by providing an actuation signal to an ejection actuator 316 or simultaneously to a group of ejection actuators 316, and measuring the weight dispensed by such an actuation signal so as to be able to determine the volume that was dispensed. Another option would be to measure the droplet size and count the number of droplets. Although the amount discharged per ejection actuator 316 or group of ejection actuators 316 may be done for each ejection actuator 316 or actuator group in any head 330 and stored on a per ejection actuator 316 or actuator group basis, the more likely option will be to evaluate a statistically significant number of ejection actuators 316 or actuator groups 316 and then assume that the others are behaving similarly. That is, after the evaluation an average will be associated with each ejection actuator 316 or group of ejection actuators 316 for the subject actuation signal. In any case, the desired discharge information can then be stored in a lookup table or the like, or stored within the controlling logic of the inhaler 320 as a number, which identifies the ejection volume per ejection actuator 316 or group of actuators 316 per actuation signal. The lookup table or stored number could be created at the time of programming the dosing event setup protocol 718, or it could be updated after each self-test has been completed and the number of operational ejection actuators 316 or groups of ejection actuators 316 has been identified.

Information that is determined or otherwise provided through execution of steps 720, 724, and 726 is used to at least in part to define a dosing event control logic. Execution of step 728 determines the number of actuation signals that will be required for the dosing event. One way in which this may be done is to divide the total dose from step 724 by the dose delivered per actuation signal per ejection actuator 316 from step 726. Thereafter, the total number of cycles required for the dosing event control logic currently being defined is determined through execution of step 730. One way in which this may be done is by dividing the number of actuation signals determined through execution of step 728 by the number of operational ejection actuators 316 determined through execution of step 720. It should be appreciated that the total number of cycles required for the current dosing event being define may utilize a fraction of a cycle.

A final parameter of the dosing event control logic that is currently be defined by the protocol 718 of FIG. 11 includes establishing the ejection actuator 316 firing frequency for each cycle of this dosing event through execution of step 732. This may be done in any appropriate manner. For instance, the operational ejection actuators 316 may be sequentially fired one at a time, groups of ejection actuators 316 may be sequentially fired one at a time, or some combination thereof. Again, there may a minimum amount of time between sequential firings of a given ejection actuator 316, which would then possibly have an effect on the firing frequency that is implemented.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

What is claimed:

1. A respiratory delivery system for at least assisting in introducing a substance to pulmonary tissue, wherein said respiratory delivery system comprises:
   at least one airflow inlet;
   at least one outlet;
   at least one airflow passage extending between said at least one airflow inlet and said at least one outlet;
   at least one ejection actuator; and
   at least one airflow regulation assembly adapted to adjust a size of a passage through which airflow is directed to achieve at least substantially the same airflow rate through said passage for inhalatory forces above a threshold.

2. A respiratory delivery system, as claimed in claim 1, wherein said respiratory delivery system is selected from the group consisting essentially of oral and nasal inhalers.

3. A respiratory delivery system, as claimed in claim 1, wherein said substance is selected from the group consisting essentially of liquid medicament and powdered medicament.

4. A respiratory delivery system, as claimed in claim 1, wherein said at least one said ejection actuator is adapted to at least assist in discharging said substance into said airflow.

5. A respiratory delivery system, as claimed in claim 1, wherein said at least one said ejection actuator comprises multiple said ejection actuators.

6. A respiratory delivery system, as claimed in claim 1, wherein each said ejection actuator is independently actuatable.

7. A respiratory delivery system, as claimed in claim 1, wherein said at least one said airflow regulation assembly is disposed at or near said at least one said airflow inlet.

8. A respiratory delivery system, as claimed in claim 1, wherein said passage comprises a flow regulation port, wherein a first inner diameter of said flow regulation port disposed toward said at least one said airflow inlet is larger than a second inner diameter of said flow regulation port disposed toward said at least one said outlet.

9. A respiratory delivery system, as claimed in claim 8, wherein side walls of said flow regulation port linearly converge in a direction of said airflow toward said at least one said outlet.

10. A respiratory delivery system, as claimed in claim 9, wherein each said airflow regulation assembly comprises a baffle comprising first and second major surfaces disposed substantially perpendicularly to a direction of said airflow and an outer periphery, wherein said outer periphery of said baffle is separated from said side walls by a first distance when said baffle is in a first position disposed toward said at least one said airflow inlet, and wherein said outer periphery of said baffle is separated from said side walls by a second distance less than said first distance when said baffle in a second position disposed toward said at least one said outlet.

11. A respiratory delivery system, as claimed in claim 1, wherein each said airflow regulation assembly comprises a baffle comprising first and second major surfaces disposed substantially perpendicularly to a direction of said airflow.

12. A respiratory delivery system, as claimed in claim 11, wherein a first position of said baffle in response to a first inhalation force is defined by said baffle being separated from said at least one said outlet by a first distance, and wherein a second position of said baffle in response to a second inhalation force greater than said first inhalation force is defined by said baffle being separated from said at least one said outlet by a second distance less than said first distance.

13. A respiratory delivery system, as claimed in claim 11, wherein a first position of said baffle in response to a first inhalation force is defined by said baffle being separated from said at least one airflow inlet by a first distance, and wherein a second position of said baffle in response to a second inhalation force greater than said first inhalation force is defined by said baffle being separated from said at least one said airflow inlet by a second distance greater than said first distance.

14. A respiratory delivery system, as claimed in claim 11, wherein said baffle avoids inhibition of said airflow in a first position disposed toward said at least one said airflow inlet, and wherein said baffle at least partially inhibits said airflow in a second position disposed toward said at least one said outlet.

15. A respiratory delivery system, as claimed in claim 11, wherein said baffle is free of holes.

16. A respiratory delivery system, as claimed in claim 11, wherein each said airflow regulation assembly comprises a biasing member comprising first and second ends, wherein said first end is disposed in contact with said baffle, wherein said second end is disposed in a fixed position relative to said at least one said airflow passage, and wherein said biasing member exerts a biasing force on said baffle in a substantially opposite direction of a direction of said airflow.

17. A respiratory delivery system, as claimed in claim 16, wherein a minimum inhalation force of a user is substantially equal in magnitude to said biasing force which is exerted on said baffle by said biasing member.

18. A respiratory delivery system, as claimed in claim 17, wherein a normal inhalation force of said user is greater than said minimum inhalation force of said user, and wherein said baffle is displaced toward said user when under effect of said normal inhalation force.

19. A respiratory delivery system, as claimed in claim 16, wherein said biasing member is a spring.

20. A respiratory delivery system, as claimed in claim 1, further comprising at least one airflow monitoring assembly adapted to monitor flow rate data.

21. A respiratory delivery system, as claimed in claim 20, wherein said at least one said airflow monitoring assembly is communicatively interconnected with said at least one said airflow regulation assembly, wherein said at least one said airflow monitoring assembly sends signals relating to said flow rate data to said at least one said airflow regulation assembly.

22. A respiratory delivery system, as claimed in claim 21, wherein said at least one said airflow regulation assembly comprises at least one passage adjustor, wherein said at least one said passage adjustor adjusts a size of said passage in response to said signals.

23. A respiratory delivery system for at least assisting in introducing a substance to pulmonary tissue, wherein said respiratory delivery system comprises:
at least one airflow inlet;
at least one outlet;
an airflow regulation port located between said at least one airflow inlet and said at least one outlet, wherein an inner wall that defines said airflow regulation port comprises an inner diameter that changes over a length of said airflow regulation port;
at least one ejection actuator for discharging said substance; and
at least one baffle movably disposed relative to said inner wall of said airflow regulation port, wherein said baffle is operative to move axially along said length of said airflow regulation port in response to inhalatory forces to alter a spacing between said baffle and said inner wall, and wherein said baffle maintains at least substantially the same airflow rate through said airflow regulation port for magnitudes of said inhalatory forces that are above a threshold.

24. A respiratory delivery system, as claimed in claim 23, wherein said inner diameter of said airflow flow regulation port at least generally converges in a direction of airflow therethrough.

25. A respiratory delivery system, as claimed in claim 24, wherein said convergence is linear.

26. A respiratory delivery system, as claimed in claim 23, wherein said baffle comprises a head having an outer periphery that is in a spaced relation to said inner wall of said airflow regulation port.

27. A respiratory delivery system, as claimed in claim 26, wherein said head defines a surface disposed substantially perpendicularly to a direction of airflow through said airflow regulation port.

28. A respiratory delivery system, as claimed in claim 26, wherein said outer periphery of said head is separated from said inner wall of said airflow regulation port by a first distance when said baffle is in a first position disposed toward said at least one airflow inlet, and wherein said outer periphery of said baffle is separated from said inner wall of said airflow regulation port by a second distance that is less than said first distance when said baffle in a second position disposed toward said at least one outlet.

29. A respiratory delivery system, as claimed in claim 23, wherein a first position of said baffle in response to a first inhalation force is defined by said baffle being separated from said at least one outlet by a first distance, and wherein a second position of said baffle in response to a second inhalation force that is greater than said first inhalation force is defined by said baffle being separated from said at least one outlet by a second distance that is less than said first distance.

30. A respiratory delivery system, as claimed in claim 23, wherein said baffle is movably supported relative to said airflow regulation port at least in part by a biasing member that biases said baffle in a direction of said at least one airflow inlet.

31. A respiratory delivery system for at least assisting in introducing a substance to pulmonary tissue, wherein said respiratory delivery system comprises:
   at least one airflow inlet;
   at least one outlet;
   at least one airflow passage extending between said at least one airflow inlet and said at least one outlet;
   a liquid medicament container;
   at least one droplet ejection assembly fluidly interconnected to said liquid medicament container, wherein said droplet ejection assembly comprises a plurality of droplet ejection orifices and a plurality of droplet ejection actuators which are independently actuatable to dispense droplets through a corresponding said droplet ejection orifice; and
   at least one airflow regulation assembly adapted to adjust a size of an airflow regulation port through which airflow is directed to achieve a substantially constant airflow rate through said airflow regulation port that is substantially independent of a magnitude of an inhalation.

* * * * *